US010799563B2

(12) United States Patent
Kurpiers et al.

(10) Patent No.: US 10,799,563 B2
(45) Date of Patent: Oct. 13, 2020

(54) POLYMERIC HGH PRODRUGS

(71) Applicant: Ascendis Pharma Endocrinology Division A/S, Hellerup (DK)

(72) Inventors: Thomas Kurpiers, Heldelberg (DE); Harald Rau, Dossenheim (DE); Evelyn Exner, Nussloch (DE); Steen Jensen, Dragoer (DK); Grethe Nørskov Rasmussen, Farum (DK); Torben Lessmann, Neustadt (DE); Thomas Wegge, Heidelberg (DE); Alina Hermann, Schriesheim (DE); Nina Schubert, Stuttgart (DE); Anna Splanemann, Heldelberg (DE); Joachim Zettler, Heidelberg (DE)

(73) Assignee: Ascendis Pharma Endocrinology Division, Hellerup (DK)

( * ) Notice: Subject to any disclaimer, the term of this patent is extended or adjusted under 35 U.S.C. 154(b) by 0 days.

(21) Appl. No.: 15/527,744

(22) PCT Filed: Nov. 17, 2015

(86) PCT No.: PCT/EP2015/076813
§ 371 (c)(1),
(2) Date: May 18, 2017

(87) PCT Pub. No.: WO2016/079114
PCT Pub. Date: May 26, 2016

(65) Prior Publication Data
US 2017/0354716 A1  Dec. 14, 2017

(30) Foreign Application Priority Data
Nov. 18, 2014 (EP) .................................... 14193603

(51) Int. Cl.
| A61K 38/27 | (2006.01) |
| A61K 47/60 | (2017.01) |
| A61K 9/08  | (2006.01) |
| A61K 47/12 | (2006.01) |
| A61K 47/20 | (2006.01) |
| A61K 47/26 | (2006.01) |
| C08G 65/334 | (2006.01) |

(52) U.S. Cl.
CPC ................ *A61K 38/27* (2013.01); *A61K 9/08* (2013.01); *A61K 47/12* (2013.01); *A61K 47/20* (2013.01); *A61K 47/26* (2013.01); *A61K 47/60* (2017.08); *C08G 65/3348* (2013.01); *C08G 2650/06* (2013.01)

(58) Field of Classification Search
CPC ........ A61K 38/27; A61K 47/12; A61K 47/20; A61K 47/26; A61K 47/60; A61K 9/08; C08G 2650/06; C08G 65/3348
See application file for complete search history.

(56) References Cited

U.S. PATENT DOCUMENTS

| 9,272,048 B2 * | 3/2016 | Rau ....................... C07K 14/61 |
| 9,511,122 B2 * | 12/2016 | Rasmussen .......... A61K 9/0019 |
| 9,919,033 B2 * | 3/2018 | Rasmussen .......... A61K 9/0019 |
| 10,098,930 B2 * | 10/2018 | Rau ....................... C07K 14/61 |
| 2012/0322721 A1 | 12/2012 | Rasmussen et al. |

FOREIGN PATENT DOCUMENTS

| EP | 1579873 | 9/2005 |
| EP | 1625855 | 2/2006 |
| EP | 2113256 | 11/2009 |
| WO | WO 2005/099768 | 10/2005 |
| WO | WO 2006/102659 | 9/2006 |
| WO | WO 2009/133137 | 11/2009 |
| WO | WO2011/073234 | * 6/2011 ............... A61K 9/14 |

OTHER PUBLICATIONS

International Search Report issued in corresponding International Application No. PCT/EP2015/076813 dated Jan. 7, 2016, 5 pages.
English Translation of International Russian Office Action issued in corresponding International Application No. 2017121203, dated May 30, 2019.

* cited by examiner

*Primary Examiner* — Marcela M Cordero Garcia
(74) *Attorney, Agent, or Firm* — Haug Partners LLP

(57) ABSTRACT

The present invention relates to a polymeric human growth hormone prodrug and dry, liquid and reconstituted pharmaceutical formulations comprising said prodrug. It furthermore relates to their use as medicaments for the treatment of diseases which can be treated with growth hormone and to methods of treatment. It also relates to methods of application of such polymeric human growth hormone prodrug or pharmaceutical formulation.

21 Claims, No Drawings

Specification includes a Sequence Listing.

POLYMERIC HGH PRODRUGS

The present application claims priority from PCT Patent Application No. PCT/EP2015/076813 filed on Nov. 17, 2015, which claims priority from European Patent Application No. EP 14193603.9 filed on Nov. 18, 2014, the disclosures of which are incorporated herein by reference in their entirety.

The present invention relates to a polymeric human growth hormone prodrug and dry, liquid and reconstituted pharmaceutical formulations comprising said prodrug. It furthermore relates to their use as medicaments for the treatment of diseases which can be treated with growth hormone and to methods of treatment. It also relates to methods of application of such polymeric human growth hormone prodrug or pharmaceutical formulation.

Human growth hormone (hGH) is a hormone that stimulates growth and cell reproduction in humans and other animals. It is a 191-amino acid, single chain polypeptide hormone which is synthesized, stored, and secreted by the somatotroph cells within the lateral wings of the anterior pituitary gland.

Growth hormone has a variety of functions in the body, the most noticeable of which is the increase of height throughout childhood, and there are several diseases which can be treated through the therapeutic use of hGH, such as for example pediatric and adult growth hormone deficiency (GHD), idiopathic short stature (ISS), short stature homeobox (SHOX) gene mutations, Turner syndrome (TS), Noonan syndrome (NS), Prader-Willi syndrome (PWS), children born small for gestational age (SGA), chronic renal insufficiency (CRI), wasting due to HIV or AIDS or other malignancies, short bowel syndrome (SBS), sarcopenia, and frailty.

Standard treatment of hGH-related diseases is via frequent, usually daily, subcutaneous injections. This is especially inconvenient for the predominantly pediatric patient population. Therefore, various approaches to provide sustained release depots requiring less frequent hGH administrations are under development, such as those described in WO2009/133137 A2.

It is also desirable to keep the injection volume low to ensure administration of the drug in a manner convenient for the patient. Injection site pain increases significantly when the injection volume is increased from 0.5 to 1.0 mL and injection volumes exceeding 1.0 mL should be avoided. As the majority of patients requiring hGH therapy are children, injection volumes should be maintained at a minimum to ensure proper compliance facilitating desired treatment outcome. The amount of hGH per given volume, however, is restricted and is lowered if certain excipients, covalently and non-covalently bound carriers, such as polymers, are used. In such cases either the administered volume per injection has to increase or more than one injection is needed. If this is not an option, certain diseases requiring higher doses of hGH, such as ISS, Turner Syndrome, Noonan Syndrome, Chronic Kidney Disease, Prader-Willi-Syndrome and pubertal GHD patients, cannot be treated with a given pharmaceutical formulation. Furthermore, pediatric patients requiring growth hormone therapy grow and gain weight and consequently require increasing amounts of hGH to ensure exposure to constant relative hGH concentrations.

It is therefore desirable to provide sustained release formulations of hGH that can be administered with a high concentration and injection volumes below 1.0 mL across different indications requiring hGH therapy.

The viscosity of a pharmaceutical formulation furthermore determines the ability to inject the pharmaceutical formulation through fine gauge needles. With increasing viscosity larger diameter needles are required to ensure that the pharmaceutical formulation can be injected within an acceptable timeframe.

As the size of the needle required for injection of said hGH formulation influences patient acceptance, it is desirable to provide sustained release formulations of hGH with a viscosity that facilitates administration with a small needle diameter and an acceptable injection time.

If a pharmaceutical formulation comprising hGH is stored in its dry form, it is desirable that the reconstitution proceeds fast and with as little foam/bubble formation as possible in order to minimize the efforts prior to administration and to ensure proper dosing of the drug.

It is therefore an object of the present invention to at least partially overcome the above-described shortcomings.

This object is achieved with a polymeric human growth hormone (hGH) prodrug or a pharmaceutically acceptable salt thereof of formula (Ia) or (Ib)

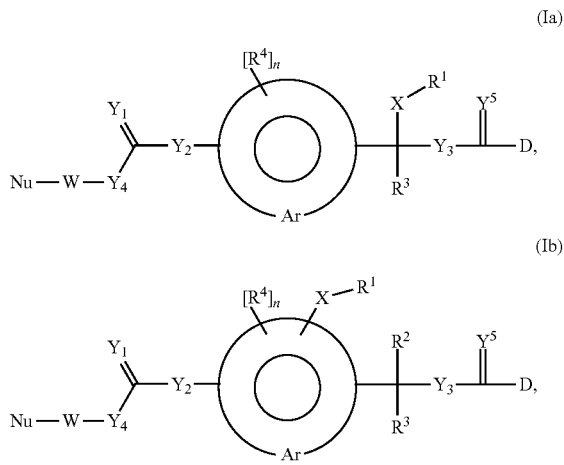

wherein
-D is a hGH moiety connected to the rest of the molecule through an amine functional group;
n is 0, 1, 2, 3, or 4;
—X— is a chemical bond or a spacer;
=$Y_1$ is selected from the group consisting of =O and =S;
—$Y_2$— is selected from the group consisting of —O— and —S—;
—$Y_3$—, —$Y_5$— are independently of each other selected from the group consisting of —O— and —S—;
—$Y_4$— is selected from the group consisting of —O—, —$NR^5$— and —$C(R^6R^{6a})$—;
—$R^1$ is a water-soluble PEG-based moiety comprising at least 40% PEG having a molecular weight ranging from 30 to 50 kDa, more preferably from 35 to 45 kDa;
—$R^2$, —$R^3$, —$R^5$, —$R^6$, —$R^{6a}$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
—$R^4$ is selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;

—W— is selected from the group consisting of $C_{1-20}$ alkyl optionally interrupted by one or more groups selected from the group consisting of $C_{3-10}$ cycloalkyl, 8- to 30-membered carbopolycyclyl, 3- to 10-membered heterocyclyl, —C(O)—, —C(O)N($R^7$)—, —O—, —S— and —N($R^7$)—;

-Nu is a nucleophile selected from the group consisting of —N($R^7 R^{7a}$), —N($R^7$OH), —N($R^7$)—N($R^{7a} R^{7b}$)), —S($R^7$), —COOH,

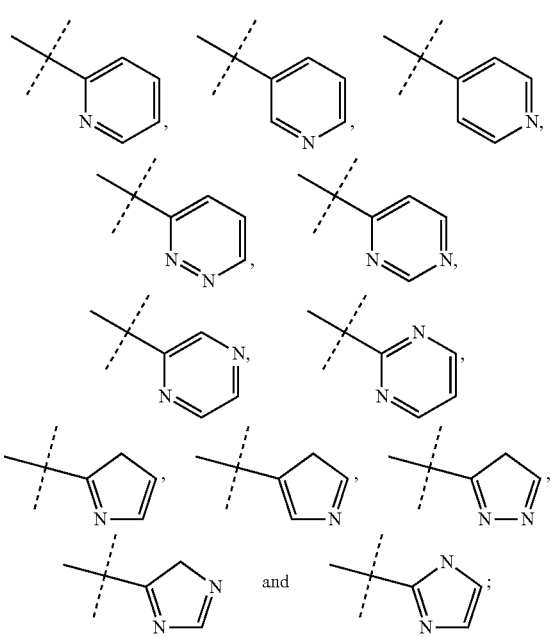

—Ar— is selected from the group consisting of

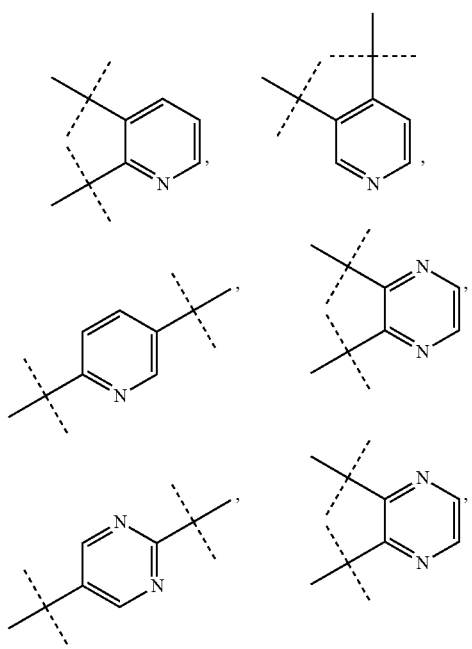

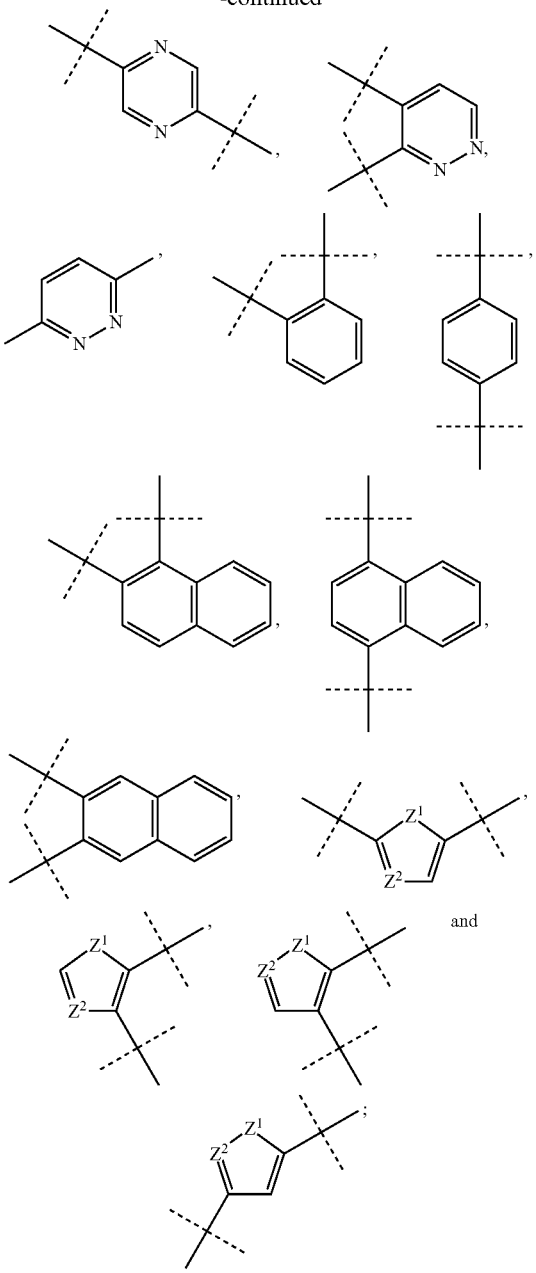

wherein
dashed lines indicate attachment to the rest of the prodrug,
—$Z^1$— is selected from the group consisting of —O—, —S— and —N($R^7$)—, and
—$Z^2$— is —N($R^7$)—; and
—$R_7$, —$R^{7a}$, —$R^{7b}$ are independently of each other selected from the group consisting of —H, $C_{1-6}$ alkyl, $C_{2-6}$ alkenyl and $C_{2-6}$ alkynyl;
wherein the prodrug of formula (Ia) and (Ib) is optionally further substituted.

It was now surprisingly found that the polymeric hGH prodrug of the present invention exhibits various unexpected properties.

It is expected that reducing the amount of PEG per hGH moiety increases the amount of hGH equivalents that can be solved in a pharmaceutical formulation with a given viscosity. However, compared to, for example, compound 36 of WO2009/133137 A2 the prodrugs of the present invention allow an increase in the relative hGH concentration that is more than proportional to the reduction of the PEG size. In other words, a pharmaceutical formulation comprising polymeric hGH prodrug with a given viscosity can comprise relatively more hGH if the polymeric hGH prodrug is of the present invention compared to, for example, compound 36 of WO2009/133137 A2.

This is advantageous, because in order to restrict the pain associated with injectable drugs limited volumes can be administered to a patient. Therefore, being able to administer more hGH per given injection volume opens up new patient populations, namely those patients suffering from diseases requiring higher hGH doses per injection and those patients suffering from diseases that may require only moderate doses per weight unit, but where the patients are heavy and thus require more hGH equivalents.

It was also surprisingly found that the polymeric hGH prodrug of the present also has surprising advantages with regard to its manufacturing process. Purification of the polymeric hGH prodrug of the present invention can be done with a loading that is at least threefold higher than for compound 36 of WO2009/133137 A2, for example, without impairing the separation efficiency and product quality. This significantly reduces the number of purifications runs needed.

Furthermore, if the prodrug of the present invention is comprised in a dry pharmaceutical formulation, said dry pharmaceutical formulation can be reconstituted faster and with the formation of less foam compared to, for example, compound 36 of WO2009/133137 A2. Therefore, reconstituting a dry pharmaceutical formulation of the present invention saves time and ensures administration of the proper dosage.

Within the present invention the terms are used with the meaning as follows:

As used herein, the term "human growth hormone (hGH)" refers all hGH polypeptides, preferably from mammalian species, more preferably from human and mammalian species, more preferably from human and murine species, as well as their variants, analogs, orthologs, homologs, and derivatives and fragments thereof, that are characterized by promoting growth in the growing phase and in maintaining normal body composition, anabolism, and lipid metabolism. Preferably, the term "hGH" refers to the hGH polypeptide of SEQ ID NO:1 as well as its variants, homologs and derivatives exhibiting essentially the same biological activity, i.e. promoting growth in the growing phase and in maintaining normal body composition, anabolism, and lipid metabolism. More preferably, the term "hGH" refers to the polypeptide of SEQ ID NO:1.

SEQ ID NO:1 has the following sequence:

```
FPTIPLSRLFDNAMLRAFIRLHQLAFDTYQEFEEAYIPKEQKYSFLQNPQ

TSLCFSESIPTPSNREETQQKSNLELLRISLLLIQSWLEPVQFLRSVFAN

SLVYGASDSNVYDLLKDLEEGIQTLMGRLEDGSPRTGQIFKQTYSKFDTN

SHNDDALLKNYGLLYCFRKDMDKVETFLRIVQCRSVEGSCGF
```

As used herein, the term "hGH polypeptide variant" refers to a polypeptide from the same species that differs from a reference hGH polypeptide. Preferably, such reference hGH polypeptide sequence is the sequence of SEQ ID NO:1. Generally, differences are limited so that the amino acid sequence of the reference and the variant are closely similar overall and, in many regions, identical. Preferably, hGH polypeptide variants are at least 70%, 80%, 90%, 95%, 96%, 97%, 98% or 99% identical to a reference hGH polypeptide, preferably the hGH polypeptide of SEQ ID NO:1. By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. These alterations of the reference sequence may occur at the amino (N-terminal) or carboxy terminal (C-terminal) positions of the reference amino acid sequence or anywhere between those terminal positions, interspersed either individually among residues in the reference sequence or in one or more contiguous groups within the reference sequence. The query sequence may be an entire amino acid sequence of the reference sequence or any fragment specified as described herein. Preferably, the query sequence is the sequence of SEQ ID NO:1.

Such hGH polypeptide variants may be naturally occurring variants, such as naturally occurring allelic variants encoded by one of several alternate forms of a hGH occupying a given locus on a chromosome or an organism, or isoforms encoded by naturally occurring splice variants originating from a single primary transcript. Alternatively, a hGH polypeptide variant may be a variant that is not known to occur naturally and that can be made mutagenesis techniques known in the art.

It is known in the art that one or more amino acids may be deleted from the N-terminus or C-terminus of a bioactive peptide or protein without substantial loss of biological function.

It is also recognized by one of ordinary skill in the art that some amino acid sequences of hGH polypeptides can be varied without significant effect of the structure or function of the protein. Such mutants include deletions, insertions, inversions, repeats, and substitutions selected according to general rules known in the art so as to have little effect on activity. For example, guidance concerning how to make phenotypically silent amino acid substitutions is provided in Bowie et al. (1990), Science 247:1306-1310, which is hereby incorporated by reference in its entirety, wherein the authors indicate that there are two main approaches for studying the tolerance of the amino acid sequence to change.

The term hGH polypeptide also encompasses all hGH polypeptides encoded by hGH analogs, orthologs, and/or species homologs. As used herein, the term "hGH analog" refers to hGH of different and unrelated organisms which perform the same functions in each organism but which did not originate from an ancestral structure that the organisms' ancestors had in common. Instead, analogous hGHs arose separately and then later evolved to perform the same or similar functions. In other words, analogous hGH polypeptides are polypeptides with quite different amino acid sequences but that perform the same biological activity, namely promoting growth in the growing phase and maintaining normal body composition, anabolism, and lipid metabolism.

As used herein the term "hGH ortholog" refers to hGH within two different species which sequences are related to each other via a common homologous hGH in an ancestral species, but which have evolved to become different from each other.

As used herein, the term "hGH homolog" refers to hGH of different organisms which perform the same functions in each organism and which originate from an ancestral structure that the organisms' ancestors had in common. In other words, homologous hGH polypeptides are polypeptides with quite similar amino acid sequences that perform the same biological activity, namely promoting growth in the growing phase and maintaining normal body composition, anabolism, and lipid metabolism. Preferably, hGH polypeptide homologs may be defined as polypeptides exhibiting at least 40%, 50%, 60%, 70%, 80%, 90%, 95%, 96%, 97%, 98% or 99% identity to a reference hGH polypeptide, preferably the hGH polypeptide of SEQ ID NO:1.

Thus, a hGH polypeptide according to the invention may be, for example: (i) one in which at least one of the amino acids residues is substituted with a conserved or non-conserved amino acid residue, preferably a conserved amino acid residue, and such substituted amino acid residue may or may not be one encoded by the genetic code; and/or (ii) one in which at least one of the amino acid residues includes a substituent group; and/or (iii) one in which the hGH polypeptide is fused with another compound, such as a compound to increase the half-life of the polypeptide (for example, polyethylene glycol); and/or (iv) one in which additional amino acids are fused to the hGH polypeptide, such as an IgG Fc fusion region peptide or leader or secretory sequence or a sequence which is employed for purification of the above form of the polypeptide or a pre-protein sequence.

The hGH polypeptide may be a monomer or multimer. Multimers may be dimers, trimers, tetramers or multimers comprising at least five monomeric polypeptide units. Multimers may also be homodimers or heterodimers. Multimers of the invention may be the result of hydrophobic, hydrophilic, ionic and/or covalent association and/or may be indirectly linked, by for example, liposome formation. Preferably, the hGH polypeptide is a monomer.

As used herein, the term "hGH polypeptide fragment" refers to any peptide or polypeptide comprising a contiguous span of a part of the amino acid sequence of a hGH polypeptide, preferably the polypeptide of SEQ ID NO:1.

More specifically, a hGH polypeptide fragment comprises at least 6, preferably at least 8 or 10, more preferably at least 12, 15, 20, 25, 30, 35, 40, 50, 60, 75, 100, 125, 150, 175, 191 consecutive amino acids of a hGH polypeptide, more preferably of the polypeptide of SEQ ID NO:1. A hGH polypeptide fragment may additionally be described as subgenuses of hGH polypeptides comprising at least 6 amino acids, wherein "at least 6" is defined as any integer between 6 and the integer representing the C-terminal amino acid of a hGH polypeptide, preferably of the polypeptide of SEQ ID No:1. Further included are species of hGH polypeptide fragments at least 6 amino acids in length, as described above, that are further specified in terms of their N-terminal and C-terminal positions. Also encompassed by the term "hGH polypeptide fragment" as individual species are all hGH polypeptide fragments, at least 6 amino acids in length, as described above, that may be particularly specified by a N-terminal and C-terminal position. That is, every combination of a N-terminal and C-terminal position that a fragment at least 6 contiguous amino acid residues in length could occupy, on any given amino acid sequence of a hGH polypeptide, preferably the hGH polypeptide of SEQ ID:NO1, is included in the present invention.

It is noted that the above species of polypeptide fragments may alternatively be described by the formula "a to b"; where "a" equals the N-terminal most amino acid position and "b" equals the C-terminal most amino acid position in the polynucleotide; and further where "a" equals an integer between 1 and the number of amino acids of a hGH polypeptide sequence minus 6, and where "b" equals an integer between 7 and the number of amino acids of the hGH polypeptide sequence; and where "a" is an integer smaller then "b" by at least 6, preferably of the hGH polypeptide sequence of SEQ ID NO:1.

The term "drug" as used herein refers to a substance used in the treatment, cure, prevention, or diagnosis of a disease or used to otherwise enhance physical or mental well-being. If a drug is conjugated to another moiety, the part of the resulting product that originated from the drug is referred to as "biologically active moiety".

As used herein the term "prodrug" refers to a biologically active moiety reversibly and covalently connected to a specialized protective group through a reversible prodrug linker moiety comprising a reversible linkage with the biologically active moiety to alter or to eliminate undesirable properties in the parent molecule. This also includes the enhancement of desirable properties in the drug and the suppression of undesirable properties. The specialized non-toxic protective group is referred to as "carrier". A prodrug releases the reversibly and covalently bound biologically active moiety in the form of its corresponding drug.

As used herein, the term "free form" of a drug means the drug in its unmodified, pharmacologically active form.

As used herein the term "liquid formulation" means a formulation comprising the polymeric hGH prodrug of the present invention and at least one solvent. A preferred solvent is water.

As used herein the term "dry formulation" means that the formulation comprising the polymeric hGH prodrug of the present invention is provided in dry form. Suitable methods for drying are spray-drying and lyophilization which is also referred to as freeze-drying. Such dry formulation comprising polymeric hGH prodrug has a residual water content of a maximum of 10%, preferably less than 5% and more preferably less than 2% which residual water content is determined according to Karl Fischer. The preferred method of drying is lyophilization. "Lyophilized formulation" means that a formulation comprising the polymeric hGH prodrug of the present invention was first frozen and subsequently subjected to water reduction by means of reduced pressure. This terminology does not exclude additional drying steps which may occur in the manufacturing process prior to filling the formulation into the final container.

As used herein the term "reconstituted formulation" means the result of adding a solvent which is also referred to as "reconstitution solution" to a dry formulation. Preferably, the amount of solvent is such that the dry formulation is completely dissolved in the resulting reconstituted formulation.

As used herein, the term "excipient" refers to a diluent, adjuvant, or vehicle with which the therapeutic is administered.

The term "water soluble" as in a "water-soluble moiety" is a moiety that is soluble in water at room temperature. Typically, a solution of a water-soluble moiety will transmit at least about 75%, more preferably at least about 95% of light, transmitted by the same solution after filtering. On weight basis, a water-soluble moiety or parts thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble moiety or parts thereof is about 95% (by weight) soluble in water or completely soluble in water.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity. Hydrogels exhibit a thermodynamic compatibility with water which allows them to swell in aqueous media.

As used herein, the term "functional group" means a group of atoms which can react with other functional groups. Functional groups include but are not limited to the following groups: carboxylic acid (—(C=O)OH), primary or secondary amine (—NH$_2$, —NH—), maleimide, thiol (—SH), sulfonic acid (—(O=S=O)OH), carbonate, carbamate (—O(C=O)N<), hydroxy (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, vinyl sulfone, vinyl ketone, diazoalkane, oxirane, and aziridine.

As used herein, the term "moiety" means a part of a molecule, which lacks at least one atom compared to the corresponding reagent. If, for example, a reagent of the formula "H—X—H" reacts with another reagent and becomes part of the reaction product, the corresponding moiety of the reaction product has the structure "H—X—" or "—X—", whereas each "—" indicates attachment to another moiety. Accordingly, a biologically active moiety is released from a prodrug as a drug.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N(R)—" can be attached to two moieties or interrupting a moiety either as "—C(O)N(R)—" or as "—N(R)C(O)—". Similarly, a moiety

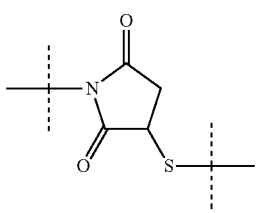

can be attached to two moieties or can interrupt a moiety either as

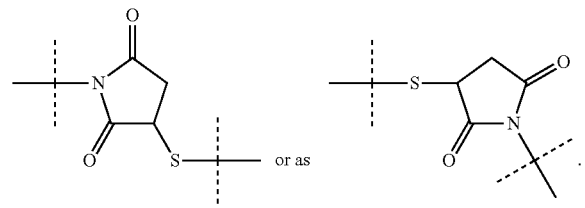

In case the compounds according to formula (Ia) and (Ib) comprise one or more acidic or basic groups, the invention also comprises their corresponding pharmaceutically or toxicologically acceptable salts, in particular their pharmaceutically utilizable salts. Thus, the compounds of formula (Ia) and (Ib) which comprise acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (Ia) and (Ib) which comprise one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charge ammonium group and an appropriate counterion of the salt. If the compounds of the formula (Ia) and (Ib) simultaneously comprise acidic and basic groups in the molecule, the invention also includes, in addition to the salt forms mentioned, inner salts or betaines zwitterions). The respective salts according to the formula (Ia) and (Ib) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (Ia) and (Ib) which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency such as the EMA (Europe) and/or the FDA (US) and/or any other national regulatory agency for use in animals, preferably in humans.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical group(s) and/or moiety/moieties, such as, for example, one or more functional group(s). Preferably, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it preferable has a molecular weight of at most 1000 kDa, such as at most 750 kDa, such as at most 500 kDa, such as at most 300 kDa, such as at most 200 kDa, such as at most 100 kDa. It is understood that for insoluble polymers, such as crosslinked hydrogels, no meaningful molecular weight ranges can be provided.

As used herein, term "polymeric" means a reagent or a moiety comprising one or more polymer(s).

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers. As used herein, the term "number average molecular weight" means the ordinary arithmetic means of the molecular weights of the individual polymers.

As used herein, the term "PEG-based comprising at least X % PEG" in relation to a moiety or reagent means that said moiety or reagent comprises at least X % (w/w) ethylene glycol units (—$CH_2CH_2O$—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

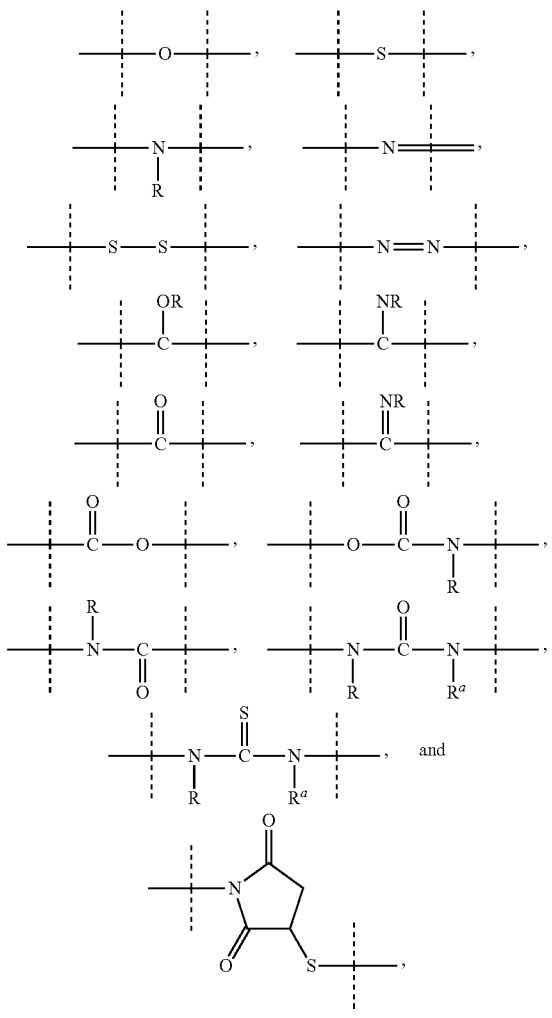

wherein
dashed lines indicate attachment to the remainder of the moiety or reagent, and R and $R^a$ are independently of each other selected from the group consisting of H, methyl, ethyl, propyl, butyl, pentyl and hexyl.

The term "substituted" as used herein means that one or more H atom(s) of a molecule or moiety are replaced by a different atom or a group of atoms, which are referred to as "substituent".

Preferably, the one or more further optional substituents are independently of each other selected from the group consisting of halogen, —CN, —COO$R^{x1}$, —O$R^{x1}$, —C(O)$R^{x1}$, —C(O)N($R^{x1}R^{x1a}$), —S(O)$_2$N($R^{x1}R^{x1a}$), —S(O)N($R^{x1}R^{x1a}$), —S(O)$_2R^{x1}$, —N($R^{x1}$)S(O)$_2$N($R^{x1a}$, $R^{x1b}$), —S$R^{x1}$, —N($R^{x1}R^{x1a}$), —NO$_2$, —OC(O)$R^{x1}$, —N($R^{x1}$)C(O)$R^{x1}$, —N($R^{x1}$)S(O)$_2R^{x1}$, —N($R^{x1}$)S(O)$R^{x1a}$, —N($R^{x1}$)C(O)O$R^{x1a}$, —N($R^{x1}$)C(O)N($R^{x1a}R^{x1b}$), —OC(O)N($R^{x1}R^{x1a}$), -$T^0$, $C_{1-50}$ alkyl, $C_{2-50}$ alkenyl, and $C_{1-50}$ alkyl, $C_{2-50}$ alkenyl, and $C_{2-50}$ alkynyl; wherein -$T^0$, $C_{1-50}$ alkyl, $C_{2-50}$ alkenyl, and $C_{2-50}$ alkynyl are optionally substituted with one or more $R^{x2}$, which are the same or different and wherein $C_{1-50}$ alkyl, $C_{2-50}$ alkenyl, and $C_{2-50}$ alkynyl are optionally interrupted by one or more groups selected from the group consisting of -$T^0$-, —C(O)O—, —O—, —C(O)—, —C(O)N($R^{x3}$)—, —S(O)$_2$N($R^{x3}$)—, —S(O)N($R^{x3}$)—, —S(O)$_2$—, —S(O)—, —N($R^{x3}$)S(O)$_2$N($R^{x3a}$)—, —S—, —N($R^{x3}$)—, —OC(O$R^{x3}$)($R^{x3a}$)—, —N($R^{x3}$)C(O)N($R^{x3a}$)—, and —OC(O)N($R^{x3}$)—;

$R^{x1}$, $R^{x1a}$, $R^{x1b}$ are independently of each other selected from the group consisting of —H, -$T^0$, $C_{1-50}$ alkyl, $C_{2-50}$ alkenyl, and $C_{2-50}$ alkynyl; wherein -$T^0$, $C_{1-50}$ alkyl, $C_{2-50}$ alkenyl, and $C_{2-50}$ alkynyl are optionally substituted with one or more $R^{x2}$, which are the same or different and wherein $C_{1-50}$ alkyl, $C_{2-50}$ alkenyl, and $C_{2-50}$ alkynyl are optionally interrupted by one or more groups selected from the group consisting of -$T^0$, —C(O)O—, —O—, —C(O)—, —C(O)N($R^{x3}$)—, —S(O)$_2$N($R^{x3}$)—, —S(O)N($R^{x3}$)—; —S(O)$_2$—, —S(O)—, —N($R^{x3}$)S(O)$_2$N($R^{x3a}$)—, —S—, —N($R^{x3}$)—, —OC(O$R^{x3}$)($R^{x3a}$)—, —N($R^{x3}$)C(O)N($R^{x3a}$)—, and —OC(O)N($R^{x3}$)—;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more $R^{x2}$, which are the same or different;

each $R^{x2}$ is independently selected from the group consisting of halogen, —CN, oxo (=O), —COO$R^{x4}$, —O$R^{x4}$, —C(O)$R^{x4}$, —C(O)N($R^{x4}R^{x4a}$), —S(O)$_2$N($R^{x4}R^{x4a}$), —S(O)N($R^{x4}R^{x4a}$), —S(O)$_2R^{x4}$, —S(O)$R^{x4}$, —N($R^{x4}$)S(O)$_2$N($R^{x4a}R^{x4b}$), —S$R^{x4}$, —N($R^{x4}R^{x4a}$), —NO$_2$, —OC(O)$R^{x4}$, —N($R^{x4}$)C(O)$R^{x4a}$, —N($R^{x4}$)S(O)$_2R^{x4a}$, —N($R^{x4}$)S(O)$R^{x4a}$, —N($R^{x4}$)C(O)O$R^{x4a}$, —N($R^{x4}$)C(O)N($R^{x4a}R^{x4b}$), —OC(O)N($R^{x4}R^{x4a}$), and $C_{1-6}$ alkyl; wherein $C_{1-6}$ alkyl is optionally substituted with one or more halogen, which are the same or different;

each $R^{x3}$, $R^{x3a}$, $R^{x4}$, $R^{x4a}$, $R^{x4b}$ is independently selected from the group consisting of —H and $C_{1-6}$ alkyl; wherein $C_{1-6}$ alkyl is optionally substituted with one or more halogen, which are the same or different.

More preferably, the one or more further optional substituents are independently of each other selected from the group consisting of halogen, —CN, —COO$R^{x1}$, —O$R^{x1}$, —C(O)$R^{x1}$, —C(O)N($R^{x1}R^{x1a}$), —S(O)$_2$N($R^{x1}R^{x1a}$), —S(O)N($R^{x1}R^{x1a}$), —S(O)$_2R^{x1}$, —S(O)$R^{x1}$, —N($R^{x1}$)S(O)$_2$N($R^{x1a}R^{x1b}$), —S$R^{x1}$, —N($R^{x1}R^{x1a}$), —NO$_2$, —OC(O)$R^{x1}$, —N($R^{x1}$)C(O)$R^{x1a}$, —N($R^{x1}$)S(O)$_2R^{x1a}$, —N($R^{x1}$)S(O)$R^{x1a}$, —N($R^{x1}$)C(O)O$R^{x1a}$, —N($R^{x1}$)C(O)N($R^{x1a}R^{x1b}$), —OC(O)N($R^{x1}R^{x1a}$), -$T^0$, $C_{1-10}$ alkyl, $C_{2-10}$ alkenyl, and $C_{2-10}$ alkynyl; wherein -$T^0$, $C_{1-10}$ alkyl, $C_{2-10}$ alkenyl, and $C_{2-10}$ alkynyl are optionally substituted with one or more $R^{x2}$, which are the same or different and wherein $C_{1-10}$ alkyl, $C_{2-10}$ alkenyl, and $C_{2-10}$ alkynyl are optionally interrupted by one or more groups selected from the group consisting of -T⁰, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3}$)—, and —OC(O)N(R$^{x3}$)—;

each $R^{x1}$, $R^{x1a}$, $R^{x1b}$, $R^{x3}$, $R^{x3a}$ is independently selected from the group consisting of —H, halogen, $C_{1-6}$ alkyl, $C_{2-6}$ alkenyl, and $C_{2-6}$ alkynyl;

each T⁰ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T⁰ is independently optionally substituted with one or more $R^{x2}$, which are the same or different;

each $R^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and $C_{1-6}$ alkyl; wherein $C_{1-6}$ alkyl is optionally substituted with one or more halogen, which are the same or different;

each $R^{x4}$, $R^{x4a}$, $R^{x4b}$ is independently selected from the group consisting of —H, halogen, $C_{1-6}$ alkyl, $C_{2-6}$ alkenyl, and $C_{2-6}$ alkynyl;

Even more preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OR(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T⁰, $C_{1-6}$ alkyl, $C_{2-6}$ alkenyl, and $C_{2-6}$ alkynyl; wherein -T⁰, $C_{1-6}$ alkyl, $C_{2-6}$ alkenyl, and $C_{2-6}$ alkynyl are optionally substituted with one or more $R^{x2}$, which are the same or different and wherein $C_{1-6}$ alkyl, $C_{2-6}$ alkenyl, and $C_{2-6}$ alkynyl are optionally interrupted by one or more groups selected from the group consisting of -T⁰, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3}$)—, —N(R$^{x3}$)C(O)N(R$^{x3a}$)—, and —OC(O)N(R$^{x3}$)—;

each $R^{x1}$, $R^{x1a}$, $R^{x1b}$, $R^{x2}$, $R^{x3}$, $R^{x3a}$ is independently selected from the group consisting of —H, halogen, $C_{1-6}$ alkyl, $C_{2-6}$ alkenyl, and $C_{2-6}$ alkynyl;

each T⁰ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T⁰ is independently optionally substituted with one or more $R^{x2}$, which are the same or different.

Preferably, a maximum of 6 —H atoms of an optionally substituted molecule or moiety are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

The term "spacer" as used herein refers preferably to a moiety selected from the group consisting of -T-, —C(O)O—, —O—, —C(O)—, —C(O)N(R$^{z1}$)—, —S(O)$_2$N(R$^{z1}$)—, —S(O)N(R$^{z1}$)—, —S(O)$_2$—, —S(O)—, —N(R$^{z1}$)S(O)$_2$N(R$^{z1a}$)—, —S—, —OC(OR$^{z1}$)(R$^{z1a}$)—, —N(R$^{z1}$)C(O)N(R$^{z1a}$)—, —OC(O)N(R$^{z1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $R^{z2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N(R$^{z3}$)—, —S(O)$_2$N(R$^{z3}$)—, —S(O)N(R$^{z3}$)—, —S(O)$_2$—, —S(O)—, —N(R$^{z3}$)S(O)$_2$N(R$^{z3a}$)—, —N(R$^{z3}$)—, —OC(OR$^{z3}$)(R$^{z3a}$)—, —N(R$^{z3}$)C(O)N(R$^{z3a}$)—, and —OC(O)N(R$^{z3}$)—;

$R^{z1}$ and $R^{z1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $R^{z2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N(R$^{z4}$)—, —S(O)$_2$N(R$^{z4}$)—, —S(O)N(R$^{z4}$)—, —S(O)$_2$—, —S(O)—, —N(R$^{z4}$)S(O)$_2$N(R$^{z4a}$)—, —S—, —N(R$^{z4}$)—, —OC(OR$^{z4}$)(R$^{z4a}$)—, —N(R$^{z4}$)C(O)N(R$^{z4a}$)—, and —OC(O)N(R$^{z4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^{z2}$, which are the same or different;

each $R^{z2}$ is independently selected from the group consisting of halogen, —CN, oxo (=O), —COOR$^{z5}$, —OR$^{z5}$, —C(O)R$^{z5}$, —C(O)N(R$^{z5}$R$^{z5a}$), —S(O)$_2$N(R$^{z5}$R$^{z5a}$), —S(O)N(R$^{z5}$R$^{z5a}$), —S(O)$_2$R$^{z5}$, —S(O)R$^{z5}$, —N(R$^{z5}$)S(O)$_2$N(R$^{z5a}$R$^{z5b}$), —SR$^{z5}$, —N(R$^{z5}$R$^{z5a}$), —NO$_2$, —OC(O)R$^{z5}$, —N(R$^{z5}$)C(O)R$^{z5a}$, —N(R$^{z5}$)S(O)$_2$R$^{z5a}$, —N(R$^{z5}$)S(O)R$^{z5a}$, —N(R$^{z5}$)C(O)OR$^{z5a}$, —N(R$^{z5}$)C(O)N(R$^{z5a}$R$^{z5b}$), —OC(O)N(R$^{z5}$R$^{z5a}$), and $C_{1-6}$ alkyl; wherein $C_{1-6}$ alkyl is optionally substituted with one or more halogen, which are the same or different;

each $R^{z3}$, $R^{z3a}$, $R^{z4}$, $R^{z4a}$, $R^{z5}$, $R^{z5a}$ and $R^{z5b}$ is independently selected from the group consisting of —H, and $C_{1-6}$ alkyl; wherein $C_{1-6}$ alkyl is optionally substituted with one or more halogen, which are the same or different.

More preferably, the term "spacer" refers to a moiety selected from the group consisting of -T-, —C(O)O—, —O—, —C(O)—, —C(O)N(R$^{z1}$)—, —S(O)$_2$N(R$^{z1}$)—, —S(O)N(R$^{z1}$)—, —S(O)$_2$—, —S(O)—, —N(R$^{z1}$)S(O)$_2$N(R$^{z1a}$)—, —S—, —N(R$^{z1}$)—, —OC(OR$^{z1}$)(R$^{z1a}$)—, —N(R$^{z1}$)C(O)N(R$^{z1a}$)—, —OC(O)N(R$^{z1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $R^{z2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N(R$^{z3}$)—, —S(O)$_2$N(R$^{z3}$)—, —S(O)N(R$^{z3}$)—, —S(O)$_2$—, —S(O)—, —N(R$^{z3}$)S(O)$_2$N(R$^{z3a}$), —N(R$^{z3}$), —OC(OR$^{z3}$)(R$^{z3a}$)—, —N(R$^{z3}$)C(O)N(R$^{z3a}$)—, and —OC(O)N(R$^{z3}$)—;

$R^{z1}$ and $R^{z1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $R^{z2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z4}$)—, —S(O)$_2$N($R^{z4}$)—, —S(O)N($R^{z4}$)—, —S(O)$_2$—, —S(O)—, —N($R^{z4}$)S(O)$_2$N($R^{z4a}$)—, —S—, —N($R^{z4}$)—, —OC(O$R^{z4}$)($R^{z4a}$)—, —N($R^{z4}$)C(O)N($R^{z4a}$), and —OC(O)N($R^{z4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^{z2}$, which are the same or different;

each $R^{z2}$ is independently selected from the group consisting of halogen, —CN, oxo (=O), —COO$R^{z5}$, —O$R^{z5}$, —C(O)$R^{z5}$, —C(O)N($R^{z5}R^{z5a}$), —S(O)$_2$N($R^{z5}R^{z5a}$), —S(O)N($R^{z5}R^{z5a}$), —S(O)$_2R^{z5}$, —S(O)$R^{z5}$, —N($R^{z5}$)S(O)$_2$N($R^{z5a}R^{z5b}$), —S$R^{z5}$, —N($R^{z5}R^{z5a}$), —NO$_2$, —OC(O)$R^{z5}$, —N($R^{z5}$)C(O)$R^{z5a}$, —N($R^{z5}$)S(O)$_2R^{z5a}$, —N($R^{z5}$)S(O)$R^{z5a}$, —N($R^{z5}$)C(O)O$R^{z5a}$, —N($R^{z5}$)C(O)N($R^{z5a}R^{z5b}$), —OC(O)N($R^{z5}R^{z5a}$), and $C_{1-6}$ alkyl; wherein $C_{1-6}$ alkyl is optionally substituted with one or more halogen, which are the same or different; and each $R^{z3}$, $R^{z3a}$, $R^{z4}$, $R^{z4a}$, $R^{z5}$, $R^{z5a}$ and $R^{z5b}$ is independently selected from the group consisting of —H, and $C_{1-6}$ alkyl, wherein $C_{1-6}$ alkyl is optionally substituted with one or more halogen, which are the same or different.

Even more preferably, the term "spacer" refers to a moiety selected from the group consisting of -T-, —C(O)O—, —O—, —C(O)—, —C(O)N($R^{z1}$)—, —S(O)$_2$N($R^{z1}$)—, —S(O)N($R^{z1}$)—, —S(O)$_2$—, —S(O)—, —N($R^{z1}$)S(O)$_2$N($R^{z1a}$)—, —S—, —N($R^{z1}$)—, —OC(O$R^{z1}$)($R^{z1a}$)—, —N($R^{z1}$)C(O)N($R^{z1a}$)—, —OC(O)N($R^{z1}$)—, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more $R^{z2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{z3}$)—, —S(O)$_2$N($R^{z3}$)—, —S(O)N($R^{z3}$)—, —S(O)$_2$—, —S(O)—, —N($R^{z3}$)S(O)$_2$N($R^{z3a}$)—, —N($R^{z3}$)—, —OC(O$R^{z3}$)($R^{z3a}$)—, —N($R^{z3}$)C(O)N($R^{z3a}$)—, and —OC(O)N($R^{z3}$)—;

$R^{z1}$ and $R^{z1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each $R^{z2}$ is independently selected from the group consisting of halogen, and $C_{1-6}$ alkyl; and each $R^{z3}$, $R^{z3a}$, $R^{z4}$, $R^{z4a}$, $R^{z5}$, $R^{z5a}$ and $R^{z5b}$ is independently of each other selected from the group consisting of —H, and $C_{1-6}$ alkyl; wherein $C_{1-6}$ alkyl is optionally substituted with one or more halogen, which are the same or different.

The term "interrupted" means that a group of atoms is inserted into a moiety between two carbon atoms or—if the insertion is at one of the moiety's ends—between a carbon and a hydrogen atom. It is understood that if a moiety is interrupted by a group of atoms at one of its ends and if the moiety that is interrupted is connected to a second moiety, the interrupting group of atoms may also be so positioned that it is located between the last atom of said moiety and the first atom of the second moiety.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—. Each hydrogen of a $C_{1-4}$ allyl may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —CH$_2$—, —CH$_2$—CH$_2$—, —CH(CH$_3$)—, —CH$_2$—CH$_2$—CH$_2$—, —CH(C$_2$H$_5$)— and —C(CH$_3$)$_2$—. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_{1-50}$ carbon may optionally be replaced by a substituent as defined above. Optionally, a $C_{1-10}$ or $C_{1-50}$ alkyl may be interrupted by one or more moieties as defined below.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —CH=CH$_2$, —CH=CH—CH$_3$, —CH$_2$—CH=CH$_2$, —CH=CHCH$_2$—CH$_3$ and —CH=CH—CH=CH$_2$. When two moieties of a molecule are linked by the $C_{2-6}$ alkenyl group, then an example for such $C_{2-6}$ alkenyl is —CH=CH—. Each hydrogen atom of a $C_{24}$, alkenyl moiety may optionally be replaced by a substituent as defined above. Optionally, a $C_{2-6}$ alkenyl may be interrupted by one or more moieties as defined below.

Accordingly, the term "$C_{2-10}$ alkenyl", "$C_{2-20}$ alkenyl" or "$C_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means straight-chain or branched hydrocarbon moiety comprising at least one carbon-carbon triple bond having 2 to 6 carbon atoms. If present at the end of a molecule, examples are —C≡CH, —CH$_2$≡CH, CH$_2$—CH$_2$—C—≡CH and CH$_2$—C≡C—CH$_3$. When two moieties of a molecule are linked by the alkynyl group, then an example is C≡C—. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-10}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkynyl or $C_{2-50}$ alkynyl may optionally be interrupted by one or more of the following moieties:

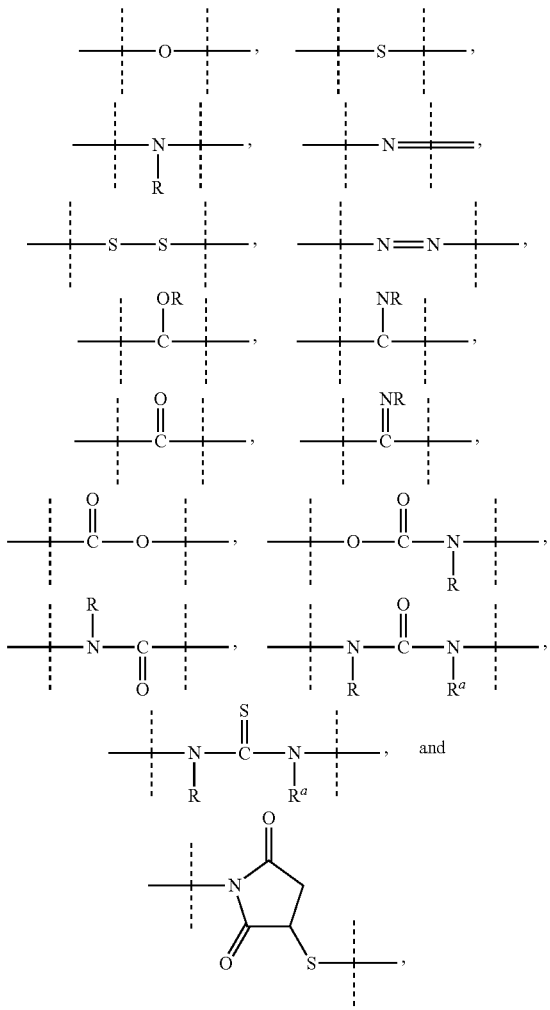

wherein
dashed lines indicate attachment to the remainder of the moiety or reagent; and
R and $R^a$ are independently of each other selected from the group consisting of H, methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may comprise up to the maximum number of double bonds (aromatic or non-aromatic ring which is fully, partially or un-saturated). Preferably a 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may comprise up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may comprise up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term "8- to 30-membered heteropolycyclyl" or "8- to 30-membered heteropolycycle" means a heterocyclic moiety of more than two rings with 8 to 30 ring atoms, preferably of three, four or five rings, where two neighboring rings share at least one ring atom and that may comprise up to the maximum number of double bonds (aromatic or non-aromatic ring which is fully, partially or unsaturated), wherein at least one ring atom up to 10 ring atoms are replaced by a heteroatom selected from the group of sulfur (including $S(O)$—, —$S(O)_2$—), oxygen and nitrogen (including =N(O)—) and wherein the ring is linked to the rest of a molecule via a carbon or nitrogen atom.

As used herein, "halogen" means fluoro, chloro, bromo or iodo. It is generally preferred that halogen is fluoro or chloro.

In general, the term "comprise" or "comprising" also encompasses "consist of" or "consisting of".

In a preferred embodiment =$Y^1$ of formula (Ia) and (Ib) is =O.

In a preferred embodiment —$Y^2$— of formula (Ia) and (Ib) is —O—.

In a preferred embodiment —$Y^3$— of formula (Ia) and (Ib) is —O—.

In a preferred embodiment —$Y^4$— of formula (Ia) and (Ib) is —$NR^5$—.

In a preferred embodiment =$Y^5$ of formula (Ia) and (Ib) is =O.

In a preferred embodiment n of formula (Ia) and (Ib) is 0 or 1. Most preferably, n of formula (Ia) and (Ib) is 0.

Preferably, $R^1$ of formula (Ia) and (Ib) is branched and comprises at least three polymeric moieties.

More preferably, $R^1$ of formula (Ia) and (Ib) comprises at least one branching point, preferably at least two branching points, and at least three polymeric chains which polymeric chains are preferably PEG-based, wherein each branching point is preferably selected from the group consisting of —N<, —$CR^8$< and >C<, wherein $R^8$ is selected from the group consisting of —H, $C_{1-6}$, alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more $R^9$, which are the same or different, and wherein $C_{1-6}$ alkyl, $C_{2-6}$ alkenyl and $C_{2-6}$ alkynyl are optionally interrupted with —C(O)O—, —O—, —C(O)—, —$C(O)N(R^{10})$—, —$S(O)_2N(R^{10})$—, —$S(O)N(R^{10})$—, —$S(O)_2$—, —S(O)—, —$N(R^{10})S(O)_2N(R^{10a})$—, —S—, —$N(R^{10})$—, —$OC(OR^{10})(R^{10a})$—, —$N(R^{10})C(O)N(R^{10a})$—, and —$OC(O)N(R^{10})$—; wherein $R^9$, $R^{10}$ and $R^{10a}$ are selected from —H, $C_{1-6}$ alkyl, $C_{2-6}$ alkenyl and $C_{2-6}$ alkynyl.

In one preferred embodiment $R^1$ of formula (Ia) and (Ib) comprises a first branching point $BP^1$ from which at least two moieties $C^1$ and $C^2$ extend of which at least one comprises an at least second branching point $BP^2$ from which at least two moieties $P^1$ and $P^2$ extend. More preferably, $R^1$ comprises a first branching point $BP^1$ from which two moieties $C^1$ and $C^2$ extend, which moiety $C^1$ comprises a branching point $BP^2$ from which at least two moieties $P^1$ and $P^2$ extend, and which moiety $C^2$ comprises a third branching point $BP^3$ from which at least two moieties $P^3$ and $P^4$ extend.

In another preferred embodiment $R^1$ comprises a moiety $C^1$ which comprises a first branching point $BP^1$, a second branching point $BP^2$ and a third branching point $BP^3$, wherein at least one moiety $P^1$ extends from $BP^1$, at least one moiety $P^2$ extends from $BP^2$ and at least one moiety $P^3$ extends from $BP^3$. More preferably, $R^1$ comprises a moiety $C^1$ which comprises a first branching point $BP^1$, a second branching point $BP^2$, a third branching point $BP^3$ and a forth branching point $BP^4$, wherein at least a moiety $P^1$ extends from $BP^1$, at least a moiety $P^2$ extends from $BP^2$, at least a moiety $P^3$ extends from $BP^3$ and at least a moiety $P^4$ extends from $BP^4$.

Preferably, $BP^1$, $BP^2$, $BP^3$ and $BP^4$ are independently of each other selected from —$CR^8$<, >C< and —N<, wherein $R^8$ is selected from —H, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more $R^9$, which are the same or different, and wherein $C_{1-6}$ alkyl, $C_{2-6}$ alkenyl and $C_{2-6}$ alkynyl are optionally interrupted with —C(O)O—, —O—, —C(O)—, —$C(O)N(R^{10})$—, —$S(O)_2N(R^{10})$—, —$S(O)N(R^{10})$—, —$S(O)_2$—, —S(O)—, —$N(R^{10})S(O)_2N(R^{10a})$—, —S—, —$N(R^{10})$—, —$OC(OR^{10})(R^{10a})$—, —$N(R^{10})C(O)N(R^{10a})$—, and —$OC(O)N(R^{10})$—; wherein $R^9$, $R^{10}$ and $R^{10a}$ are selected from —H, $C_{1-6}$ alkyl, $C_{2-6}$ alkenyl and $C_{2-6}$ alkynyl.

Preferably, $C^1$ and $C^2$ are independently of other selected from $C_{1-50}$ alkyl, $C_{2-50}$ alkenyl and $C_{2-50}$ alkynyl; wherein $C_{1-50}$ alkyl, $C_{2-50}$ alkenyl and $C_{2-50}$ alkynyl are optionally substituted with one or more $R^{11}$, which are the same or different, and wherein $C_{1-50}$ alkyl, $C_{2-50}$ alkenyl and $C_{2-50}$ alkynyl are optionally interrupted with one or more groups selected from the group consisting of -T-, —C(O)O—, —O—, —C(O)—, —$C(O)N(R^{12})$—, —$S(O)_2N(R^{12})$—, —$S(O)N(R^{12})$—, —$S(O)_2$—, —S(O)—, —$N(R^{12})S(O)_2N(R^{12a})$—, —S—, —$N(R^{12})$—, —$OC(OR^{12})(R^{12a})$—, —$N(R^{12})C(O)N(R^{12a})$—, and —$OC(O)N(R^{12})$—;

wherein -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, and wherein each -T- is independently optionally substituted with one or more $R^{11}$, which are the same or different;

wherein each $R^{11}$ is independently selected from the group consisting of halogen, —CN, oxo (=O), —$COOR^{12}$, —$OR^{12}$, —$C(O)R^{12}$, —$C(O)N(R^{12}R^{12a})$, —$S(O)_2N(R^{12}R^{12a})$, —$S(O)N(R^{12}R^{12a})$, —$S(O)_2R^{12}$, —$S(O)R^{12}$, —$N(R^{12})S(O)_2N(R^{12a}R^{12b})$, —$SR^{12}$, —$N(R^{12}R^{12a})$, —$NO_2$, —$OC(O)R^{12}$, —$N(R^{12})C(O)R^{12a}$, —$N(R^{12})S(O)_2R^{12a}$, —$N(R^{12})S(O)R^{12a}$, —$N(R^{12})C(O)OR^{12a}$, —$N(R^{12})C(O)N(R^{12a}R^{12b})$, —$OC(O)N(R^{12}R^{12a})$, and $C_{1-6}$ alkyl; wherein $C_{1-6}$ alkyl is optionally substituted with one or more halogen, which are the same or different;

and wherein each $R^{12}$, $R^{12a}$ and $R^{12b}$ are independently of each other selected from the group consisting of —H, $C_{1-6}$ alkyl, $C_{2-6}$ alkenyl and $C_{2-6}$ alkynyl, wherein $C_{1-6}$ alkyl, $C_{2-6}$ alkenyl and $C_{2-6}$ alkynyl is optionally substituted with one or more halogen, which are the same or different.

Preferably, $P^1$, $P^2$, $P^3$, $P^4$ are independently of each other a polymeric moiety, more preferably a PEG-based chain comprising at least 40% PEG, even more preferably at least 50% PEG, even more preferably at least 60% PEG, even more preferably at least 70% PEG, even more preferably at least 80% PEG, even more preferably at least 90% PEG and most preferably at least 95% PEG.

Preferably, $P^1$, $P^2$, $P^3$, $P^4$ have independently of each other a molecular weight of at least 5 kDa, such as 7.5 kDa, 10 kDa, 12 kDa or 15 kDa.

In a preferred embodiment —R¹ of formula (Ia) and (Ib) comprises a moiety of formula (II)

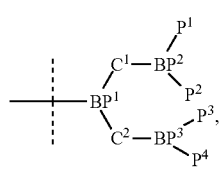
(II)

wherein
—BP¹<, —BP²<, —BP³< are independently of each other selected from the group consisting of —N< and —C(R⁸)<;
R⁸ is selected from the group consisting of H, $C_{1-6}$ alkyl, $C_{2-6}$ alkenyl and $C_{2-6}$ alkynyl;
—P¹, —P², —P³, —P⁴ are independently of each other a PEG-based chain comprising at least 40% PEG and having a molecular weight ranging from 8 to 12 kDa;
—C¹—, —C²— are independently of each other selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more R⁹, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N(R¹⁰), —S(O)₂N(R¹⁰)—, —S(O)N(R¹⁰)—, —S(O)₂—, —S(O)—, —N(R¹⁰)S(O)₂N(R¹⁰ᵃ)—, —S—, —N(R¹⁰)—, —OC(OR¹⁰)(R¹⁰ᵃ)—, —N(R¹⁰)C(O)N(R¹⁰ᵃ) and —OC(O)N(R¹⁰)—;
each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more R⁹, which are the same or different;
each R⁹ is independently selected from the group consisting of halogen, —CN, oxo (=O), —COOR¹¹, —OR¹¹, —C(O)R¹¹, —C(O)N(R¹¹R¹¹ᵃ), —S(O)₂N(R¹¹R¹¹ᵃ), —S(O)N(R¹¹R¹¹ᵃ), —S(O)₂R¹¹, —S(O)R¹¹, —N(R¹¹)S(O)₂N(R¹¹ᵃR¹¹ᵇ), —SR¹¹, —N(R¹¹R¹¹ᵃ), —NO₂, —OC(O)R¹¹, —N(R¹¹)C(O)R¹¹ᵃ, —N(R¹¹)S(O)₂R¹¹ᵃ, —N(R¹¹)S(O)R¹¹ᵃ, —N(R¹¹)C(O)OR¹¹ᵃ, —N(R¹¹)C(O)N(R¹¹ᵃR¹¹ᵇ), —OC(O)N(R¹¹R¹¹ᵃ), and $C_{1-6}$ alkyl; wherein $C_{1-6}$ alkyl is optionally substituted with one or more halogen, which are the same or different; and
each R¹⁰, R¹⁰ᵃ, R¹¹, R¹¹ᵃ and R¹¹ᵇ is independently selected from the group consisting of —H, and $C_{1-6}$ alkyl, wherein $C_{1-6}$ alkyl is optionally substituted with one or more halogen, which are the same or different.
In a preferred embodiment BP¹ of formula (II) is —N<.
In a preferred embodiment BP² and BP² of formula (II) are both —CH<.
It is advantageous if the first branching point BP¹ and the attachment site of X are separated by no more than a certain number of atoms.
Preferably, the critical distance in the prodrugs of the present invention is less than 60 atoms, more preferably less than 50 atoms, even more preferably less than 40 atoms, even more preferably less than 30 atoms, even more preferably less than 20 atoms and most preferably less than 10 atoms.

The term "critical distance" refers to the shortest distance measured as the number of atoms between the first branching point BP¹ comprised in R¹ and the atom marked with the asterisk in formula (a), if the prodrug of the present invention is of formula (Ia), or refers to the number of atoms between the first branching point BP¹ comprised in R¹ and the atom marked with the asterisk in formula (b), if the prodrug of the present invention is of formula (Ib):

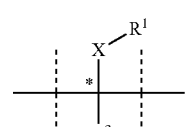
(a)

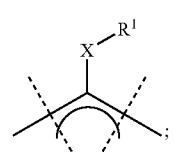
(b)

wherein the dashed lines indicate attachment to the remainder of the prodrug of formula (Ia) in the case of (a) and to the remainder of the prodrug of formula (Ib) in the case of (b).

In a preferred embodiment C¹ and C² of formula (II) are $C_{1-50}$ alkyl interrupted by one or more of the groups selected from the group consisting of —O—, —C(O)N(R¹⁰)— and 3- to 10 membered heterocyclyl; wherein the 3- to 10 membered heterocyclyl is substituted with at least one oxo (=O).

Most preferably, C¹ and C² of formula (II) are of formula (IIa)

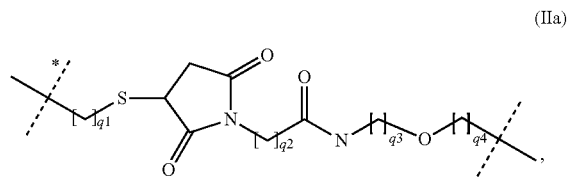
(IIa)

wherein
the dashed line marked with the asterisk indicates attachment to BP¹;
the unmarked dashed line indicates attachment to BP² or BP³, respectively;
q1 is 1, 2, 3, 4, 5, 6, 7 or 8; preferably q1 is 4, 5, 6, 7, or 8; more preferably q1 is 5, 6 or 7; most preferably q1 is 6;
q2 is 1, 2, 3, 4, or 5; preferably q2 is 1, 2 or 3; most preferably q2 is 2;
q3 is 1, 2, 3, 4, 5, 6, 7 or 8; preferably q3 is 2, 3, 4, or 5; more preferably q3 is 2, 3 or 4; most preferably q3 is 3;
q4 is 1, 2 or 3; most preferably, q4 is 1.
In a preferred embodiment P¹, P², P³ and P⁴ of formula (II) are independently of each other of formula (IIb)

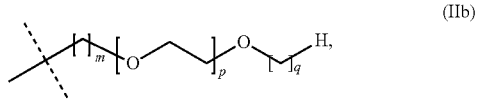

wherein the dashed line indicates attachment the remainder of $R^1$, i.e. to $BP^2$ or $BP^3$, respectively, m is 0 or 1, p is an integer ranging from 180 to 270, more preferably 200 to 250, even more preferably 210 to 240, most preferably 220 to 240, and q is selected from the group consisting of 1, 2, 3, 4, 5, and 6.

More preferably, —R' comprises a moiety of formula (IIc):

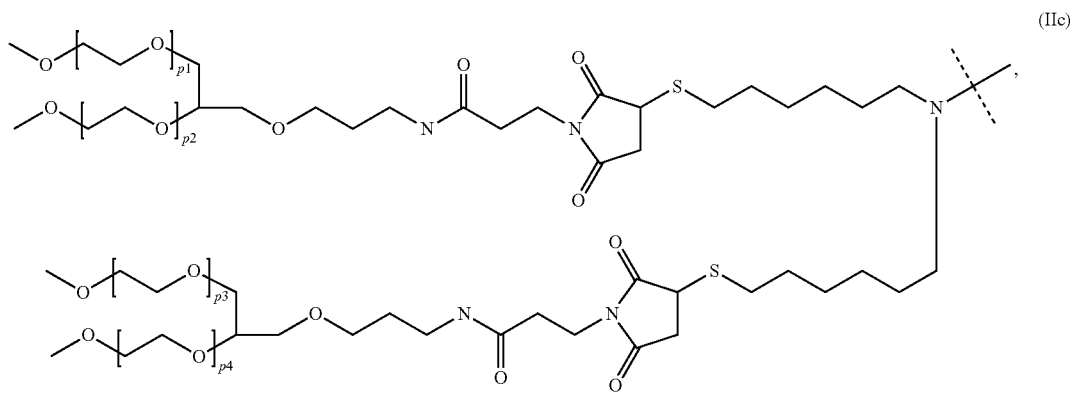

wherein p1, p2, p3, p4 are independently an integer ranging from 180 to 270, preferably from 200 to 250, even more preferably from 210 to 240 and most preferably from 220 to 240.

In a preferred embodiment —$R^2$ of formula (Ib) is selected from the group consisting of —H, methyl, ethyl, n-propyl, isopropyl, n-butyl, isobutyl, sec-butyl and tert-butyl. More preferably, —$R^2$ of formula (Ib) is selected from the group consisting of —H, methyl, ethyl, n-propyl and isopropyl. Even more preferably —$R^2$ of formula (Ib) is selected from —H, methyl and ethyl. Most preferably, —$R^2$ of formula (Ib) is —H.

In a preferred embodiment —$R^3$ of formula (Ia) and (Ib) is selected from the group consisting of —H, methyl, ethyl, n-propyl, isopropyl, n-butyl, isobutyl, sec-butyl and test-butyl. More preferably, —$R^3$ of formula (Ia) and (Ib) is selected from the group consisting of —H, methyl, ethyl, n-propyl and isopropyl. Even more preferably —$R^3$ of formula (Ia) and (Ib) is selected from —H, methyl and ethyl. Most preferably, —$R^3$ of formula (Ia) and (Ib) is —H.

In a preferred embodiment, each —$R^4$ of formula (Ia) and (Ib) is independently selected from methyl, ethyl, n-propyl, isopropyl, n-butyl, isobutyl, sec-butyl and tert-butyl. More preferably, —$R^4$ of formula (Ia) and (Ib) is selected from the group consisting of methyl, ethyl, n-propyl and isopropyl. Even more preferably —$R^4$ of formula (Ia) and (Ib) is selected from methyl and ethyl.

In a preferred embodiment —$R^5$ of formula (Ia) and (Ib) is selected from the group consisting of —H, methyl, ethyl, n-propyl, isopropyl, n-butyl, isobutyl, sec-butyl and tert-butyl. More preferably, —$R^5$ of formula (Ia) and (Ib) is selected from the group consisting of —H, methyl, ethyl, n-propyl and isopropyl. Even more preferably —$R^5$ of formula (Ia) and (Ib) is selected from methyl and ethyl. Most preferably, —$R^5$ of formula (Ia) and (Ib) is methyl.

In a preferred embodiment —$R^6$ and —$R^{6a}$ of formula (Ia) and (Ib) are independently selected from the group consisting of —H, methyl, ethyl, n-propyl, isopropyl, n-butyl, isobutyl, sec-butyl and tert-butyl. More preferably, —$R^6$ and —$R^{6a}$ of formula (Ia) and (Ib) are independently selected from the group consisting of —H, methyl, ethyl, n-propyl and isopropyl. Even more preferably —$R^6$ and —$R^{6a}$ of formula (Ia) and (Ib) are independently selected from —H, methyl and ethyl. Most preferably, —$R^6$ and —$R^{6a}$ of formula (Ia) and (Ib) are both —H.

In a preferred embodiment X of formula (Ia) and (Ib) is preferably selected from the group consisting of -T-, —C(O)O—, —O—, —C(O)—, —C(O)N($R^{z1}$)—, —S(O)$_2$N($R^{z1}$)—, —S(O)N($R^{z1}$)—, —S(O)$_2$—, —S(O)—, —N($R^{z1}$)S(O)$_2$N($R^{z1a}$)—, —S—, —OC(O$R^{z1}$)($R^{z1a}$)—, —N($R^{z1}$)C(O)N($R^{z1a}$)—, —OC(O)N($R^{z1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $R^{z2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —C(O)—, —C(O)N($R^{z3}$)—, —S(O)$_2$N($R^{z3}$)—, —S(O)N($R^{z3}$)—, —S(O)$_2$—, —S(O)—, —N($R^{z3}$)S(O)$_2$N($R^{z3a}$)—, —S—, —N($R^{z3}$)—, —OC($R^{z3}$)($R^{z3a}$)—, —N($R^{z3}$)C(O)N($R^{z3a}$)—, and —OC(O)N($R^{z3}$)—;

$R^{z1}$ and $R^{z1a}$ are independently of each other selected from the group consisting of —H, -T, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $R^{z2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z4}$)—, —S(O)$_2$N($R^{z4}$)—, —S(O)N($R^{z4}$)—, —S(O)$_2$—, —S(O)—, —N($R^{z4}$)S(O)$_2$N($R^{z4a}$)—, —S—, —N($R^{z4}$)—, —OC(O$R^{z4}$)($R^{z4a}$)—, —N($R^{z4}$)C(O)N($R^{z4a}$)—, and —OC(O)N($R^{z4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^{z2}$, which are the same or different;

each $R^{z2}$ is independently selected from the group consisting of halogen, —CN, oxo (=O), —COO$R^{z5}$, —O$R^{z5}$, —C(O)$R^{z5}$, —C(O)N($R^{z5}R^{z5a}$), —S(O)$_2$N($R^{z5}R^{z5a}$), —S(O)N($R^{z5}R^{z5a}$), —S(O)$_2R^{z5}$, —S(O)$R^{z5}$, —N($R^{z5}$)S(O)$_2$N($R^{z5a}R^{z5b}$), —S$R^{z5}$, —N($R^{z5}R^{z5a}$), —NO$_2$, —OC(O)$R^{z5}$, —N($R^{z5}$)C(O)$R^{z5a}$, —N($R^{z5}$)S(O)$_2R^{z5a}$, —N($R^{z5}$)S(O)$R^{z5a}$, —N($R^{z5}$)C(O)O$R^{z5a}$, —N($R^{z5}$)C(O)N($R^{z5a}R^{z5b}$), —OC(O)N($R^{z5}R^{z5a}$), and $C_{1-6}$, alkyl; wherein $C_{1-6}$ alkyl is optionally substituted with one or more halogen, which are the same or different;

each $R^{z3}$, $R^{z3a}$, $R^{z4}$, $R^{z4a}$, $R^{z5}$, $R^{z5a}$ and $R^{z5b}$ is independently selected from the group consisting of —H, and $C_{1-6}$ alkyl; wherein $C_{1-6}$ alkyl is optionally substituted with one or more halogen, which are the same or different.

More preferably, X of formula (Ia) and (Ib) is selected from the group consisting of $C_{1-10}$ alkyl, $C_{2-10}$ alkenyl, and $C_{2-10}$ alkynyl; wherein $C_{1-10}$ alkyl, $C_{2-10}$ alkenyl, and $C_{2-10}$ alkynyl are optionally substituted with one or more $R^{z2}$, which are the same or different and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{z3}$)—, —S(O)$_2$N($R^{z3}$)—, —S(O)N($R^{z3}$)—, —S(O)$_2$—, —S(O)—, —N($R^{z3}$)S(O)$_2$N($R^{z3a}$)—, —S—, —N($R^{z3}$)—, —OC(O$R^{z3}$)($R^{z3a}$)—, —N($R^{z3}$)C(O)N($R^{z3a}$)—, and —OC(O)N($R^{z3}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^{z2}$, which are the same or different;

each $R^{z2}$ is independently selected from $C_{1-6}$ alkyl, wherein $C_{1-6}$ alkyl is optionally substituted with one or more halogen, which are the same or different;

each $R^{z3}$, $R^{z3a}$ is independently selected from the group consisting of —H, and $C_{1-6}$ alkyl, wherein $C_{1-6}$ alkyl is optionally substituted with one or more halogen, which are the same or different.

Even more preferably, X of formula (Ia) and (Ib) is $C_{1-10}$ alkyl which is optionally interrupted by one or more groups selected from the group consisting of —C(O)O—, —O—, —C(O)—, —C(O)N($R^{z3}$)—, —S—, —N($R^{z3}$)—, —OC(O$R^{z3}$)($R^{z3a}$)— and —OC(O)N($R^{z3}$)—;

each $R^{z3}$, $R^{z3a}$ is independently selected from —H and $C_{1-6}$ alkyl.

Most preferably, X of formula (Ia) and (Ib) is of formula (III)

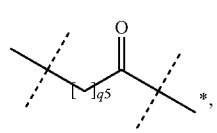

(III)

wherein the dashed line marked with the asterisk indicates attachment to the $R^1$;

the unmarked dashed line indicates attachment to remainder of the prodrug;

q5 is 1, 2, 3, 4, 5, 6, 7 or 8; preferably q5 is 1, 2, 3, 4, or 5; more preferably q5 is 2, 3 or 4; most preferably q5 is 3;

Preferably, Ar of formula (Ia) and (Ib) is phenyl. Most preferably Ar of formula (Ia) and (Ib) is

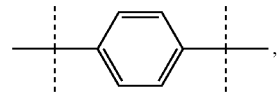

wherein the dashed lines indicate attachment to the remainder of the prodrug of formula (Ia) or (Ib).

Preferably W of formula (Ia) and (Ib) is $C_{1-20}$ alkyl, optionally interrupted with $C_{3-10}$ cycloalkyl, —C(O)—, —C(O)N($R^7$)—, —O—, —S— and —N($R^7$)—. Even more preferably, W of formula (Ia) and (Ib) is $C_{1-10}$ alkyl, optionally interrupted with $C_{3-10}$ cycloalkyl, —C(O)—, —C(O)N($R^7$)—, —O—, —S— and —N($R^7$)—. Even more preferably, W of formula (Ia) and (Ib) is $C_{1-6}$ alkyl, optionally interrupted with $C_{3-10}$ cycloalkyl, —C(O)—, —C(O)N($R^7$)—, —O—, —S— and —N($R^7$)—. Most preferably, W of formula (Ia) and (Ib) is

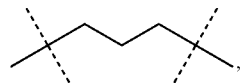

wherein the dashed lines indicate attachment to the rest of the molecule.

Preferably, —Nu of formula (Ia) and (Ib) is —N($R^7R^{7a}$).

Preferably, —$R^7$ and —$R^{7a}$ of formula (Ia) and (Ib) are independently of each other selected from the group consisting of —H, methyl, ethyl, n-propyl, isopropyl, n-butyl, isobutyl, sec-butyl and tert-butyl. More preferably, —$R^7$ and —$R^{7a}$ of formula (Ia) and (Ib) are independently of each other selected from —H, methyl, ethyl, n-propyl and isopropyl. Even more preferably, —$R^7$ and —$R^{7a}$ of formula (Ia) and (Ib) are independently of each other selected from methyl or ethyl. Most preferably, —$R^7$ and —$R^{7a}$ of formula (Ia) and (Ib) are both methyl.

Most preferably, the polymeric hGH prodrug of the present invention is of formula (IV)

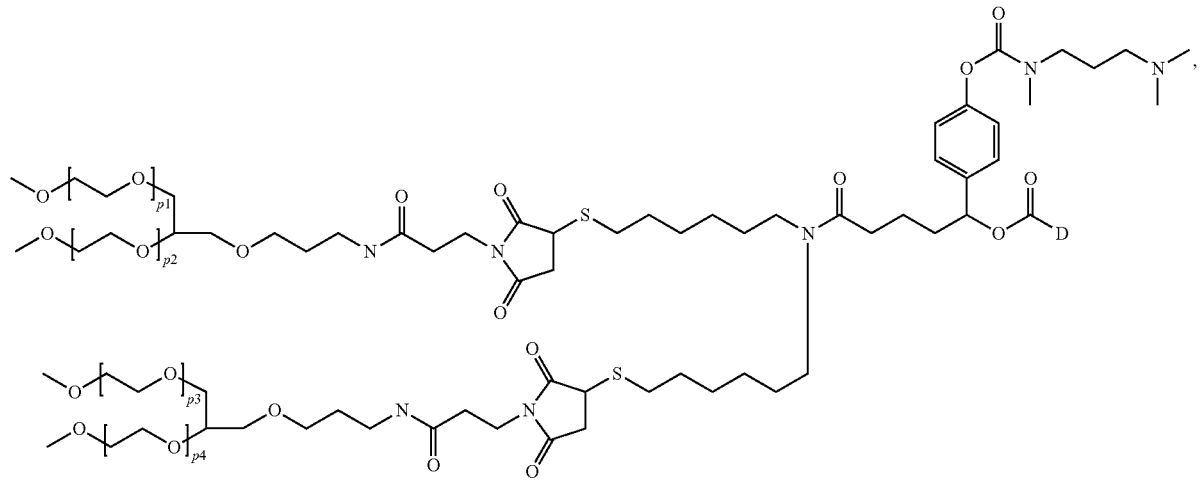

(IV)

wherein

D is a hGH moiety connected to the rest of the molecule through an amine functional group; and p1, p2, p3, p4 are independently an integer ranging from 180 to 270, preferably from 200 to 250, even more preferably from 210 to 240 and most preferably from 220 to 240.

Most preferably, D of formula (IV) is connected to the rest of the molecule through an amine provided by a lysine side chain.

Another aspect of the present invention is a pharmaceutical formulation comprising at least one polymeric hGH prodrug of the present invention and at least one excipient. Preferably, the at least one polymeric hGH prodrug of the present invention is of formula (IV).

In one embodiment the pharmaceutical formulation is a liquid formulation comprising at least one polymeric hGH prodrug of the present invention and at least one excipient. Preferably, the at least one polymeric hGH prodrug of the present invention is of formula (IV).

Preferably, such liquid formulation comprises from 3 to 300 mg/mL of the polymeric hGH prodrug of the present invention, preferably of the polymeric hGH prodrug of formula (IV) (corresponding to 1 to 100 mg hGH equivalents/mL). More preferably the liquid formulation comprises from 9 to 150 mg/mL polymeric hGH prodrug of the present invention, preferably of the polymeric hGH prodrug of formula (IV) (corresponding to 3 to 50 mg hGH equivalents/mL). Even more preferably the liquid formulation comprises from 15 to 120 mg/mL polymeric hGH prodrug of the present invention, preferably of the polymeric hGH prodrug of formula (IV) (corresponding to 5 to 40 mg hGH equivalents/mL). Even more preferably the liquid formulation comprises from 30 to 45 mg/mL polymeric hGH prodrug of the present invention, preferably of the polymeric hGH prodrug of formula (IV) (corresponding to 10 to 15 mg hGH equivalents/mL) or equally preferably the liquid formulation comprises from 75 to 105 mg/mL polymeric hGH prodrug of the present invention, preferably of the polymeric hGH prodrug of formula (IV) (corresponding to 25 to 30 mg hGH equivalents/mL). In a particularly preferred embodiment thereof, the liquid formulation comprises 42 or 84 mg/mL of the polymeric hGH prodrug of the present invention, preferably of the polymeric hGH prodrug of formula (IV) (corresponding to 14 or 28 mg hGH equivalents/mL).

The liquid formulation of polymeric hGH prodrug according to the present invention may comprise one or more excipients. Excipients used in parenteral formulations may be categorized as, for example, buffering agents, isotonicity modifiers, preservatives, stabilizers, anti-adsorption agents, oxidation protection agents, viscosifiers/viscosity enhancing agents, or other auxiliary agents. However, in some cases, one excipient may have dual or triple functions. The liquid formulation may comprise one or more than one of the following excipients:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used.

(ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum.

(iii) Preservatives and/or antimicrobials: multidose parenteral formulations require the addition of preservatives at a sufficient concentration to minimize risk of patients becoming infected upon injection and corresponding regulatory requirements have been established. Typical preservatives include in-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride.

(iv) Stabilizers: Stabilisation is achieved by strengthening of the protein-stabilising forces, by destabilisation of the denatured state, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used.

(v) Anti-adsorption agents: Mainly ionic or non-ionic surfactants or other proteins or soluble polymers are used to coat or adsorb competitively to the inner surface of the formulation's container. E.g., poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically a monolayer of surfactant is formed at the interface just above the CMC value.

(vi) Oxidation protection agents: antioxidants such as ascorbic acid, ectoine, methionine, glutathione, monothioglycerol, morin, polyethylenimine (PEI), propyl gallate, and vitamin E. Chelating agents such as citric acid, EDTA, hexaphosphate, and thioglycolic acid may also be used.

(vii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue. A spreading agent such as but not limited to hyaluronidase temporarily decreases the viscosity of the extracellular matrix and promotes diffusion of injected drugs.

(viii) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture The liquid formulation of polymeric hGH prodrug according to the present invention comprises one or more buffering agents. Preferred are such buffering agents which have a pharmaceutically sufficient buffer capacity in the desired pH range. In a preferred embodiment thereof the buffering agent is selected from the group consisting of sodium phosphate, bicarbonate, succinate, histidine, citrate and acetate. Most preferably the buffering agent is succinate. Usually the pH is adjusted by using succinic acid in a concentration of 5-50 mM, more preferably in a concentration of 10 mM and titrating the solution with Tris-base, more preferably with a 1 molar Tris-base solution to the desired pH.

In a preferred embodiment the pH of a liquid formulation of the present invention ranges from pH 1 to pH 10, more preferably ranges from pH 3 to pH 7, even more preferably ranges from pH 4 to pH 6, even more preferably ranges from pH 4.5 to 5.5 and most preferably has a pH of 5.0. Preferably a buffer concentration and pH is chosen to minimize hGH release during storage, as well as to minimize deamidation, aggregation and precipitation of hGH.

Preferably, the liquid formulation of polymeric hGH prodrug of the present invention comprises one or more oxidation protection agent such as antioxidants or chelating agents. A preferred antioxidant is methionine.

In one embodiment the liquid formulation of the present invention comprises trehalose.

In one embodiment the liquid formulation of the present invention comprises one or more preservative and/or antimicrobial, such as, for example benzylalcohol and/or cresol.

In one embodiment the liquid formulation of the present invention comprises the polymeric hGH prodrug of the present invention, preferably the polymeric hGH prodrug of formula (IV) an oxidation protection agent and a buffering agent, even more preferably the polymeric hGH prodrug of formula (IV), an oxidation protection agent, a stabilizer and a buffering agent.

Preferably, the liquid formulation of the present invention comprises the polymeric hGH prodrug of the present invention, preferably the polymeric hGH prodrug of formula (IV), methionine and succinate, even more preferably the polymeric hGH prodrug of formula (IV), methionine, succinate and trehalose, optionally as dihydrate.

Optionally, the liquid formulation of the present invention also comprises benzylalcohol and/or cresol.

Preferably, the liquid formulation of the present invention comprises

| polymeric hGH prodrug | 3-300 mg/ml |
|---|---|
| succinic acid | 5-50 mM |
| optionally trehalose dihydrate | 25-150 mg/ml |
| optionally methionine | 1-50 mM | and has a pH ranging from pH 4.0 to pH 6.0 which is titrated using a suitable buffer, preferably using Tris-base, more preferably using a 1 molar Tris-base solution; and wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 1-100 mg hGH equivalents/ml.

More preferably, the liquid formulation of the present invention comprises

| polymeric hGH prodrug | 3-300 mg/ml |
|---|---|
| succinic acid | 5-50 mM |
| optionally trehalose dihydrate | 50-90 mg/ml |
| optionally methionine | 1-50 mM | and has a pH ranging from pH 4.0 to pH 6.0 which is titrated using a suitable buffer, preferably using Tris-base, more preferably using a 1 molar Tris-base solution; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 1-100 mg hGH equivalents/ml.

More preferably, the liquid formulation of the present invention comprises

| polymeric hGH prodrug | 9-150 mg/ml |
|---|---|
| succinic acid | 5-50 mM |
| optionally trehalose dihydrate | 50-90 mg/ml |
| optionally methionine | 1-50 mM | and has a pH ranging from pH 4.0 to pH 6.0 which is titrated using a suitable buffer, preferably using Tris-base, more preferably using a 1 molar Tris-base solution; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 1-100 mg hGH equivalents/ml.

Even more preferably, the liquid formulation of the present invention comprises

| polymeric hGH prodrug | 15-120 mg/ml |
|---|---|
| succinic acid | 5-40 mM |
| optionally trehalose dihydrate | 60-86 mg/ml |
| optionally methionine | 5-40 mM | and has a pH ranging from pH 4.0 to pH 6.0 which is titrated using a suitable buffer, preferably using Tris-base, more preferably using a 1 molar Tris-base solution; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 5-40 mg hGH equivalents/ml.

Even more preferably, the liquid formulation of the present invention comprises

| polymeric hGH prodrug | 30-45 mg/ml |
| succinic acid | 5-20 mM |
| optionally trehalose dihydrate | 75-86 mg/ml |
| optionally methionine | 5-20 mM | and has a pH ranging from pH 4.5 to pH 5.5 which is titrated using a suitable buffer, preferably using Tris-base, more preferably using a 1 molar Tris-base solution; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 10-15 mg hGH equivalents/ml.

In an equally preferred embodiment, the liquid formulation of the present invention comprises

| polymeric hGH prodrug | 75-105 mg/ml |
| succinic acid | 5-20 mM |
| optionally trehalose dihydrate | 60-81 mg/ml |
| optionally methionine | 5-20 mM | and has a pH ranging from pH 4.5 to pH 5.5 which is titrated using a suitable buffer, preferably using Tris-base, more preferably using a 1 molar Tris-base solution; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 25-35 mg hGH equivalents/ml.

In a preferred embodiment, the liquid formulation comprising at least one polymeric hGH prodrug of the present invention, preferably of formula (IV), comprises

| polymeric hGH prodrug | 42 mg/ml |
| succinic acid | 10 mM |
| optionally trehalose dihydrate | 79-86 mg/ml |
| optionally methionine | 10 mM | and has a pH ranging from pH 4.5 to pH 5.5 which is titrated using a suitable buffer, preferably using Tris-base, more preferably using a 1 molar Tris-base solution; wherein the polymeric hGH prodrug is the polymeric hGH prodrug of the present invention, preferably the polymeric prodrug of formula (IV). If the polymeric hGH prodrug is of formula (IV), the amount of polymeric hGH prodrug corresponds to 14 mg hGH equivalents/ml.

In another preferred embodiment the liquid formulation comprising at east one polymeric prodrug of the present invention, preferably of formula (IV), comprises

| polymeric hGH prodrug | 84 mg/ml |
| succinic acid | 10 mM |

-continued

| optionally trehalose dihydrate | 70-80 mg/ml |
| optionally methionine | 10 mM | and has a pH ranging from pH 4.5 to pH 5.5 which is titrated using a suitable buffer, preferably using Tris-base, more preferably using a 1 molar Tris-base solution; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 28 mg hGH equivalents/ml.

In one embodiment the liquid formulation of the present invention comprises at least one further biologically active agent, either in its free form or as a prodrug, and wherein the at least one further biologically active agents is preferably selected from the group consisting of IGF-1, ghrelin and ghrelin-like compounds, gonadotropin releasing hormone agonists, gonadotropin releasing hormone analogs, growth hormone releasing factor, growth hormone releasing factor analogs, gonadal steroids, antiandrogens, non-steroidal aromatase inhibitors, HIV combination therapy, free fatty acid regulators, anabolic steroids, estrogen agonists and antagonists, propranolol, appetite suppressants, osteoporosis drugs (including bisphosphonates, bone formation agents, estrogens, parathyroid hormones, selective receptor modulators, and/or anti-diabetic drugs such as insulin, thiazolidinediones, sulfonyl ureas, incretin memetics, meglitinides, biguanides, alpha-glucosidase inhibitors and amylin analogues). Preferably, the at least one additional biological active agent is in its free form.

In another embodiment the pharmaceutical formulation of the present invention is a dry formulation.

Preferably, such dry pharmaceutical formulation comprises from 1 to 99.9% (w/w), more preferably from 1.9 to 89% (w/), even more preferably from 3 to 83% (w/w), even more preferably from 9.0 to 71% (w/w), even more preferably from 15 to 63% (w/w), even more preferably from 26 to 36% (w/w) or from 48 to 62% (w/w) and most preferably from 32 to 34% (w/w) or 50 to 54% (w/w) of the polymeric hGH prodrug of the present invention, preferably of polymeric hGH prodrug of formula (IV).

Preferably, the dry pharmaceutical formulation of the present invention comprises at least one lyoprotectant. The at least one lyoprotectant is preferably selected from the group consisting of amino acids, methylamines, lyotropic salts, polyols, propylene glycol, polyethylene glycol, pluronics, hydroxyalkyl starches, and combinations thereof.

If the lyoprotectant is an amino acid it is preferably selected from the group consisting of monosodium glutamate and histidine.

If the lyoprotectant is a polyol, it is preferably selected from the group consisting of sucrose, trehalose, glycerin, erythritol, glycerol, arabitol, xylitol, sorbitol and mannitol.

If the lyoprotectant is a methylamine it is preferably betaine.

If the lyoprotectant is a lyotropic salt, it is preferably magnesium sulfate.

If the lyoprotectant is a hydroxyalkyl starch, it is preferably hydroxyethyl starch.

In a preferred embodiment, the lyoprotectant is a non-reducing sugar. Even more preferably, the lyoprotectant is trehalose or sucrose. Most preferably the lyoprotectant is trehalose.

Preferably, the dry pharmaceutical formulation of the present invention comprises from 8 to 97% (w/w), more preferably from 14 to 96% (w/w), even more preferably from 24 to 90% (w/w), even more preferably from 32 to 84% (w/w), even more preferably from 60 to 73% (w/w) or from 35 to 52% (w/w) and most preferably 64-66% (w/w) or 45-48% (w/w) of the at least one lyoprotectant, preferably trehalose dihydrate.

Preferably, the dry formulation of the present invention comprises at least one buffering agent. Preferably the buffering agent is selected from the group consisting of sodium phosphate, bicarbonate, succinate, histidine, citrate and acetate. Most preferably the buffering agent is succinate. Preferably the pH is adjusted by using succinic acid in a concentration of 5-50 mM, more preferably in a concentration of 10 mM and titrating the solution with Tris-base, more preferably with a 1 molar Tris-base solution to the desired pH.

Preferably, the dry formulation is obtained by a process comprising the steps of (a) Providing a liquid formulation comprising

| | |
|---|---|
| polymeric hGH prodrug | 3-300 mg/ml |
| succinic acid | 5-50 mM |
| optionally trehalose dihydrate | 25-150 mg/ml | and having a pH ranging from pH 4.0 to pH 6.0 which is titrated using a suitable buffer, preferably using Tris-base, more preferably using a 1 molar Tris-base solution;
and wherein the polymeric hGH prodrug is the polymeric hGH prodrug of the present invention, preferably the polymeric hGH prodrug of formula (IV); and (b) Drying the liquid formulation of step (a).

More preferably, the liquid formulation of step (a) comprises

| | |
|---|---|
| polymer hGH prodrug | 3-300 mg/ml |
| succinic acid | 5-50 mM |
| optionally trehalose dihydrate | 50-90 mg/ml | and has a pH ranging from pH 4.0 to pH 6.0 which is titrated using a suitable buffer, preferably using Tris-base, more preferably using a 1 molar Tris-base solution; and wherein the polymeric hGH prodrug is the polymeric hGH prodrug of the present invention, preferably the polymeric hGH prodrug of formula (IV).

More preferably, the liquid formulation of step (a) comprises

| | |
|---|---|
| polymer hGH prodrug | 9-150 mg/ml |
| succinic acid | 5-50 mM |
| optionally trehalose dihydrate | 50-90 mg/ml | and has a pH ranging from pH 4.0 to pH 6.0 which is titrated using a suitable buffer, preferably using Tris-base, more preferably using a 1 molar Tris-base solution; and wherein the polymeric hGH prodrug is the polymeric hGH prodrug of the present invention, preferably the polymeric hGH prodrug of formula (IV).

Even more preferably, the liquid formulation of step (a) comprises

| | |
|---|---|
| polymeric hGH prodrug | 15-120 mg/ml |
| succinic acid | 5-40 mM |
| optionally trehalose dihydrate | 60-86 mg/ml | and has a pH ranging from pH 4.0 to pH 6.0 which is titrated using a suitable buffer, preferably using Tris-base, more preferably using a 1 molar Tris-base solution; and wherein the polymeric hGH prodrug is the polymeric hGH prodrug of the present invention, preferably the polymeric hGH prodrug of formula (IV).

Even more preferably, the liquid formulation of step (a) comprises

| | |
|---|---|
| polymeric hGH prodrug | 30-45 mg/ml |
| succinic acid | 5-20 mM |
| optionally trehalose dihydrate | 75-86 mg/ml | and has a pH ranging from pH 4.5 to pH 5.5 which is titrated using a suitable buffer, preferably using Tris-base, more preferably using a 1 molar Tris-base solution; and wherein the polymeric hGH prodrug is the polymeric hGH prodrug of the present invention, preferably the prodrug of formula (IV).

Even more preferably, the liquid formulation of step (a) comprises

| | |
|---|---|
| polymeric hGH prodrug | 75-105 mg/ml |
| succinic acid | 5-20 mM |
| optionally trehalose dihydrate | 60-81 mg/ml | and has a pH ranging from pH 4.5 to pH 5.5 which is titrated using a suitable buffer, preferably using Tris-base, more preferably using a 1 molar Tris-base solution; and wherein the polymeric hGH prodrug is the polymeric hGH prodrug of the present invention, preferably the polymeric hGH prodrug of formula (IV).

Most preferably, the liquid formulation of step (a) comprises

| | |
|---|---|
| polymeric hGH prodrug | 42 mg/ml |
| succinic acid | 10 mM |
| optionally trehalose dihydrate | 79-86 mg/ml | and has a pH ranging from pH 4.5 to pH 5.5 which is titrated using a suitable buffer, preferably using Tris-base, more preferably using a 1 molar Tris-base solution; and wherein the polymeric hGH prodrug is the polymeric hGH prodrug of the present invention, preferably the polymeric hGH prodrug of formula (IV).

In an equally preferred embodiment, the liquid formulation of step (a) comprises

| | |
|---|---|
| polymeric hGH prodrug | 84 mg/ml |
| succinic acid | 10 mM |
| optionally trehalose dihydrate | 70-80 mg/ml, | and has a pH ranging from pH 4.5 to pH 5.5 which is titrated using a suitable buffer, preferably using Tris-base, more preferably using a 1 molar Tris-base solution; and wherein the polymeric hGH prodrug is the polymeric hGH prodrug of the present invention, preferably the polymeric hGH prodrug of formula (IV).

Preferably, in step (b) the liquid formulation is dried by lyophilization.

In one embodiment the formulation of step (a) comprises at least one further biologically active agent, either in its free form or as a prodrug, and wherein the at least one further biologically active agents is selected from the group consisting of IGF-1, ghrelin and ghrelin-like compounds, gonadotropin releasing hormone agonists, gonadotropin releasing hormone analogs, growth hormone releasing factor, growth hormone releasing factor analogs, gonadal steroids, antiandrogens, non-steroidal aromatase inhibitors, HIV combination therapy, free fatty acid regulators, anabolic steroids, estrogen agonists and antagonists, propranolol, appetite suppressants, osteoporosis drugs (including bisphosphonates, bone formation agents, estrogens, parathyroid hormones, selective receptor modulators, and/or antidiabetic drugs such as insulin, thiazolidinediones, sulfonyl ureas, incretin memetics, meglitinides, biguanides, alpha-glucosidase inhibitors and amylin analogues). Preferably, the at least one additional biological active agent is in its free form.

Another aspect of the present invention is a dry formulation comprising based on the total weight of the formulation:

| | |
|---|---|
| polymeric hGH prodrug | 2-89% (w/w) |
| succinic acid | 0.4-1.8% (w/w) |
| trehalose dihydrate | 7-97% (w/w) |
| Tris | 0.4-2% (w/w) | wherein the polymeric hGH prodrug is the polymeric hGH prodrug of the present invention, preferably the polymeric hGH prodrug of formula (IV).

In an preferred embodiment the dry formulation of the present invention comprises based on the total weight of the formulation:

| | |
|---|---|
| polymeric hGH prodrug | 3-83% (w/w) |
| succinic acid | 0.6-1.6% (w/w) |
| trehalose dihydrate | 14-96% (w/w) |
| Tris | 0.6-1.7% (w/w) | wherein the polymeric hGH prodrug is the polymeric hGH prodrug of the present invention, preferably the polymeric hGH prodrug of formula (IV).

In an even more preferred embodiment the dry formulation of the present invention comprises based on the total weight of the formulation:

| | |
|---|---|
| polymeric hGH prodrug | 9.0-71% (w/w) |
| succinic acid | 0.6-2.8% (w/w) |
| trehalose dihydrate | 24-90% (w/w) |
| Tris | 0.6-2.9% (w/w) | wherein the polymeric prodrug is the polymeric prodrug of the present invention, preferably the polymeric hGH prodrug of formula (IV).

In an even more preferred embodiment the dry formulation of the present invention comprises based on the total weight of the formulation:

| | |
|---|---|
| polymeric hGH prodrug | 15-63% (w/w) |
| succinic acid | 0.6-2.5% (w/w) |
| trehalose dihydrate | 32-84% (w/w) |
| Tris | 0.6-2.6% (w/w) | wherein the polymeric hGH prodrug is the polymeric hGH prodrug of the present invention, preferably the polymeric hGH prodrug of formula (IV).

In an even more preferred embodiment the dry formulation of the present invention comprises based on the total weight of the formulation:

| | |
|---|---|
| polymeric hGH prodrug | 26-36% (w/w) |
| succinic acid | 0.5-1.9% (w/w) |
| trehalose dihydrate | 60-73% (w/w) |
| Tris | 0.5-1.9% (w/w) | wherein the polymeric hGH prodrug is the polymeric hGH prodrug of the present invention, preferably the polymeric hGH prodrug of formula (IV).

In an equally preferred embodiment the dry formulation of the present invention comprises based on the total weight of the formulation:

| | |
|---|---|
| polymeric hGH prodrug | 48-62% (w/w) |
| succinic acid | 0.4-1.4% (w/w) |
| trehalose dihydrate | 35-52% (w/w) |
| Tris | 0.4-1.4% (w/w) | wherein the polymeric hGH prodrug is the polymeric hGH prodrug of the present invention, preferably the polymeric hGH prodrug of formula (IV).

Most preferably the dry formulation of the present invention comprises based on the total weight of the formulation:

| | |
|---|---|
| polymeric hGH prodrug | 32-34% (w/w) |
| succinic acid | 0.9-1.0% (w/w) |
| trehalose dihydrate | 64-66% (w/w) |
| Tris | 0.5-1.4% (w/w) | wherein the polymeric hGH prodrug is the polymeric hGH prodrug of the present invention, preferably the polymeric hGH prodrug of formula (IV).

In an equally preferred embodiment the dry formulation of the present invention comprises based on the total weight of the formulation:

| | |
|---|---|
| polymeric hGH prodrug | 50-54 (w/w) |
| succinic acid | 0.7-0.8% (w/w) |
| trehalose dihydrate | 45-48% (w/w) |
| Tris | 0.4-1.1% (w/w) | wherein the polymeric hGH prodrug is the polymeric hGH prodrug of the present invention, preferably the polymeric hGH prodrug of formula (IV).

In one embodiment the dry formulations of the present invention comprise at least one further biologically active agent, either in its free form or as a prodrug, and wherein the at least one further biologically active agents is selected from the group consisting of IGF-1, ghrelin and ghrelin-like compounds, gonadotropin releasing hormone agonists, gonadotropin releasing hormone analogs, growth hormone releasing factor, growth hormone releasing factor analogs, gonadal steroids, antiandrogens, non-steroidal aromatase inhibitors, HIV combination therapy, free fatty acid regulators, anabolic steroids, estrogen agonists and antagonists, propranolol, appetite suppressants, osteroporosis drugs (including bisphosphonates, bone formation agents, estrogens, parathyroid hormones, selective receptor modulators, and/or anti-diabetic drugs such as insulin, thiazolidinediones, sulfonyl ureas, incretin memetics, meglitinides, biguanides, alpha-glucosidase inhibitors and amylin analogues). Preferably, the at least one additional biological active agent is in its free form.

Preferably, the dry formulation of the present invention is obtained from lyophilization.

Preferably, the dry formulation of the present invention is lyophilized in a vial, syringe, dual-chamber syringe, ampoule, cartridge or dual-chamber cartridge.

A preferred vial is a glass vial.

In one embodiment the dry formulation of the present invention is lyophilized in a cartridge for use in a pen injector.

In another embodiment, the dry formulation is lyophilized in a first chamber of a dual-chamber cartridge, of which second chamber is filled with reconstitution solution.

Prior to administering the dry formulation of the present invention to a patient in need thereof, the dry formulation is reconstituted. Reconstitution can take place in the container in which the dry formulation of polymeric hGH prodrug of the present invention is provided, such as in a vial, syringe, dual-chamber syringe, ampoule, cartridge and dual-chamber cartridge, or the dry formulation of the present invention is transferred to a different container and is then reconstituted.

Reconstitution is done by adding a predefined amount of reconstitution solution to the dry formulation. The reconstitution solution is a sterile liquid, such as water or buffer, which may comprise further additives, such as preservatives and/or antimicrobials.

In one embodiment the reconstitution solution is sterile water comprising 0.7-1.1% benzyl alcohol, more preferably comprising 0.9% benzyl alcohol. In another embodiment, the reconstitution solution is sterile water comprising 0.2-0.4% cresol, more preferably comprising 0.3% cresol. Preferably, the reconstitution solution is sterile water.

Preferably, the pH of the reconstituted formulation of the present invention ranges from pH 1 to pH 10, more preferably ranges from pH 3 to pH 7, even more preferably ranges from pH 4 to pH 6, even more preferably ranges from pH 4.5 to 5.5 and most preferably has a pH of 5.0.

Another aspect of the present invention is a method of preparing a reconstituted formulation comprising the polymeric hGH prodrug of the present invention, wherein the method comprises the step of
contacting the dry pharmaceutical formulation of the present invention with a reconstitution solution.

Another aspect of the present invention is a reconstituted formulation obtainable from the method of preparing a reconstituted formulation of the present invention.

Preferably, the reconstituted formulation of the present invention comprises

| polymeric hGH prodrug | 3-300 mg/ml |
| succinic acid | 5-50 mM |
| trehalose dihydrate | 25-150 mg/ml |
| Tris | 1-50 mM | and has a pH ranging from pH 4.0 to pH 6.0; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 1-100 mg hGH equivalents/ml.

Even more preferably, the reconstituted formulation of the present invention comprises

| polymeric hGH prodrug | 3-300 mg/ml |
| succinic acid | 5-50 mM |
| trehalose dihydrate | 50-90 mg/ml |
| Tris | 5-50 mM | and has a pH ranging from pH 4.0 to pH 6.0; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 1-100 mg hGH equivalents/ml.

In an even more preferred embodiment the reconstituted formulation of the present invention comprises

| polymeric hGH prodrug | 9-150 mg/ml |
| succinic acid | 5-50 mM |
| trehalose dihydrate | 50-90 mg/ml |
| Tris | 5-50 mM | and has a pH ranging from pH 4.0 to pH 6.0; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 3-50 mg hGH equivalents/ml.

In an even more preferred embodiment the reconstituted formulation of the present invention comprises

| polymeric hGH prodrug | 15-120 mg/ml |
| succinic acid | 5-40 mM |
| trehalose dihydrate | 60-86 mg/ml |
| Tris | 5-40 mM | and has a pH ranging from pH 4.0 to pH 6.0; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 5-40 mg hGH equivalents/ml.

Even more preferably, the reconstituted formulation of be present invention comprises

| polymeric hGH prodrug | 30-45 mg/ml |
| succinic acid | 5-20 mM |
| trehalose dihydrate | 75-86 mg/ml |
| Tris | 5-20 mM | and has a pH ranging from pH 4.5 to pH 5.5; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 10-15 mg hGH equivalents/ml.

In an equally preferred embodiment, the reconstituted formulation of the present invention comprises

| | |
|---|---|
| polymeric hGH prodrug | 75-105 mg/ml |
| succinic acid | 5-20 mM |
| trehalose dihydrate | 60-81 mg/ml |
| Tris | 5-20 mM | and has a pH ranging from pH 4.5 to pH 5.5; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 25-35 mg hGH equivalents/ml.

Most preferably the reconstituted formulation of the present invention comprises

| | |
|---|---|
| polymeric hGH prodrug | 42 mg/ml |
| succinic acid | 10 mM |
| trehalose dihydrate | 79-86 mg/ml, |
| Tris | 5-15 mM | and has a pH ranging from pH 4.5 to pH 5.5; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 14 mg hGH equivalents/ml.

In an equally preferred embodiment the reconstituted formulation of the present invention comprises

| | |
|---|---|
| polymeric hGH prodrug | 84 mg/ml |
| succinic acid | 10 mM |
| trehalose dihydrate | 70-80 mg/ml |
| Tris | 5-15 mM | and has a pH ranging from pH 4.5 to pH 5.5; wherein the polymeric hGH prodrug is the polymeric hGH prodrug of the present invention, preferably the polymeric hGH prodrug of formula (IV). If the polymeric hGH prodrug is of formula (IV), the amount of polymeric hGH prodrug corresponds to 28 mg hGH equivalents/ml.

Optionally, the reconstituted formulation comprises one or more preservative and/or antimicrobial. Preferably, the one or more preservative and/or antimicrobial is benzyl alcohol in a concentration of 0.7-1.1% (w/v), more preferably in a concentration of 0.9% (w/v). In another embodiment, the one or more preservative and/or antimicrobial is cresol in a concentration of 0.2-0.4% (w/v), more preferably in a concentration of 0.3% (w/v).

The person skilled in the art is well aware that whenever a dry, liquid or reconstituted formulation of the present invention comprises trehalose dihydrate, the dihydrate form could also be exchanged by other hydration forms of trehalose, including anhydrous trehalose. The skilled artisan would have no difficulty in calculating the corresponding amounts of trehalose in these other hydration forms including anhydrous trehalose comprised in the corresponding dry, liquid or reconstituted formulation. Therefore, it is understood that a dry, liquid or reconstituted formulation comprising trehalose in hydration forms other than dihydrate are also within the scope of the present invention.

Another aspect of the present invention is the polymeric hGH prodrug of the present invention, preferably of formula (IV), or the liquid, dry or reconstituted pharmaceutical formulation comprising at least one polymeric hGH prodrug of the present invention, preferably of formula (IV), for use as a medicament.

Another aspect of the present invention is the use of the polymeric hGH prodrug of the present invention, preferably the polymeric hGH prodrug of formula (IV), or the liquid, dry or reconstituted pharmaceutical formulation comprising at least one polymeric hGH prodrug of the present invention, preferably comprising the polymeric hGH prodrug of formula (IV), in a method of treatment of a disease which can be treated with hGH.

Preferably, said disease which can be treated with hGH is selected from the group consisting of growth hormone deficiency (GHD) in children, idiopathic short stature (ISS), short stature homeobox (SHOX) gene mutations, Turner syndrome (TS), Noonan syndrome (NS), Prader-Willi syndrome (PWS), children born small for gestational age (SGA), chronic renal insufficiency (CRI), growth hormone deficiency (GHD) in adults, wasting due to HIV or AIDS or other malignancies, short bowel syndrome (SBS), sarcopenia, and frailty.

In one embodiment the disease which can be treated with hGH is GHD in children.

In another embodiment the disease which can be treated with hGH is GHD in adults.

In another embodiment the disease which can be treated with hGH is ISS.

In another embodiment the disease which can be treated with hGH are SHOX gene mutations.

In another embodiment the disease which can be treated with hGH is TS.

In another embodiment the disease which can be treated with hGH is NS.

In another embodiment the disease which can be treated with hGH is PWS.

In another embodiment the disease which can be treated with hGH is SGA.

In another embodiment the disease which can be treated with hGH is CRI.

In another embodiment the disease which can be treated with hGH is wasting due to HIV or AIDS or other malignancies.

In another embodiment the disease which can be treated with hGH is SBS.

In another embodiment the disease which can be treated with hGH is sarcopenia.

In another embodiment the disease which can be treated with hGH is frailty.

Another aspect of the present invention is the use of the polymeric hGH prodrug, preferably the polymeric hGH prodrug of formula (IV), or the liquid, dry or reconstituted pharmaceutical formulation comprising at least one polymeric hGH prodrug of the present invention, preferably comprising the polymeric hGH prodrug of formula (IV), for the manufacture of a medicament for treating a disease which can be treated with hGH.

Preferably, said disease which can be treated with hGH is selected from the group consisting of GHD in children, ISS, SHOX gene mutations, TS, NS, PWS, SGA, CRI, GHD in adults, wasting clue to HIV or AIDS or other malignancies, SBS, sarcopenia, and frailty.

In one embodiment the polymeric hGH prodrug, preferably the polymeric hGH prodrug of formula (IV), or the liquid, dry or reconstituted pharmaceutical formulation of the present invention is used for the manufacture of a medicament for treating GHD in children.

In another embodiment the polymeric hGH prodrug, preferably the polymeric hGH prodrug of formula (IV), or the liquid, dry or reconstituted pharmaceutical formulation of the present invention is used for the manufacture of a medicament for treating GHD in adults.

In another embodiment the polymeric hGH prodrug, preferably the polymeric hGH prodrug of formula (IV), or the liquid, dry or reconstituted pharmaceutical formulation of the present invention is used for the manufacture of a medicament for treating ISS.

In another embodiment the polymeric hGH prodrug, preferably the polymeric hGH prodrug of formula (IV), or the liquid, dry or reconstituted pharmaceutical formulation of the present invention is used for the manufacture of a medicament for treating SHOX gene mutations.

In another embodiment the polymeric hGH prodrug, preferably the polymeric hGH prodrug of formula (IV), or the liquid, dry or reconstituted pharmaceutical formulation of the present invention is used for the manufacture of a medicament for treating TS.

In another embodiment the polymeric hGH prodrug, preferably the polymeric hGH prodrug of formula (IV), or the liquid, dry or reconstituted pharmaceutical formulation of the present invention is used for the manufacture of a medicament for treating NS.

In another embodiment the polymeric hGH prodrug, preferably the polymeric hGH prodrug of formula (IV), or the liquid, dry or reconstituted pharmaceutical formulation of the present invention is used for the manufacture of a medicament for treating PWS.

In another embodiment the polymeric hGH prodrug, preferably the polymeric hGH prodrug of formula (IV), or the liquid, dry or reconstituted pharmaceutical formulation of the present invention is used for the manufacture of a medicament for treating SGA.

In another embodiment the polymeric hGH prodrug, preferably the polymeric hGH prodrug of formula (IV), or the liquid, dry or reconstituted pharmaceutical formulation of the present invention is used for the manufacture of a medicament for treating CRI.

In another embodiment the polymeric hGH prodrug, preferably the polymeric hGH prodrug of formula (IV), or the liquid, dry or reconstituted pharmaceutical formulation of the present invention is used for the manufacture of a medicament for treating wasting due to HIV or AIDS or other malignancies.

In another embodiment the polymeric hGH prodrug, preferably the polymeric hGH prodrug of formula (IV), or the liquid, dry or reconstituted pharmaceutical formulation of the present invention is used for the manufacture of a medicament for treating SBS.

In another embodiment the polymeric hGH prodrug, preferably the polymeric hGH prodrug of formula (IV), or the liquid, dry or reconstituted pharmaceutical formulation of the present invention is used for the manufacture of a medicament for treating sarcopenia.

In another embodiment the polymeric hGH prodrug, preferably the polymeric hGH prodrug of formula (IV), or the liquid, dry or reconstituted pharmaceutical formulation of the present invention is used for the manufacture of a medicament for treating frailty.

Another aspect of the present invention is a method of treating, controlling, delaying or preventing, preferably of treating, in a mammalian patient, preferably a human patient, in need of the treatment, control, delay or prevention of at least one diseases which can be treated, controlled, delayed or prevented with hGH, wherein the method comprises the step of administering to said patient in need thereof a therapeutically effective amount of polymeric hGH prodrug of the present invention, preferably of formula (IV), or the liquid, dry or reconstituted formulation comprising at least one polymeric hGH prodrug of the present invention, preferably comprising the polymeric hGH prodrug of formula (IV).

Preferably, the at least one disease which can be treated with hGH is selected from the group consisting of GHD in children, ISS, SHOX gene mutations, TS, NS, PWS, SGA, CRI, GHD in adults, wasting due to HIV or AIDS or other malignancies, SBS, sarcopenia, and frailty.

In one embodiment the disease which can be treated with hGH with the method of treating, controlling, delaying or preventing of the present invention is GHD in children.

In another embodiment the disease which can be treated with hGH with the method of treating, controlling, delaying or preventing of the present invention is GHD in adults.

In one embodiment the disease which can be treated with hGH with the method of treating, controlling, delaying or preventing of the present invention is ISS.

In one embodiment the disease which can be treated with hGH with the method of treating, controlling, delaying or preventing of the present invention is SHOX gene mutations.

In one embodiment the disease which can be treated with hGH with hod of treating, controlling, delaying or preventing of the present invention is TS.

In one embodiment the disease which can be treated with hGH with the method of treating, controlling, delaying or preventing of the present invention is NS.

In one embodiment the disease which can be treated with hGH with the method of treating, controlling, delaying or preventing of the present invention is PWS.

In one embodiment the disease which can be treated with hGH with the method of treating, controlling, delaying or preventing of the present invention is SGA.

In one embodiment the disease which can be treated with hGH with the method of treating, controlling, delaying or preventing of the present invention is CRI.

In one embodiment the disease which can be treated with hGH with the method of treating, controlling, delaying or preventing of the present invention is wasting due to HIV or AIDS or other malignancies.

In one embodiment the disease which can be treated with hGH with the method of treating, controlling, delaying or preventing of the present invention is SBS.

In one embodiment the disease which can be treated with hGH with the method of treating, controlling, delaying or preventing of the present invention is sarcopenia.

In one embodiment the disease which can be treated with hGH with the method of treating, controlling, delaying or preventing of the present invention is frailty.

Another aspect of the present invention is a method of administering the polymeric hGH prodrug or the liquid or reconstituted formulation of the present invention, wherein the method comprises the step of administering the polymeric hGH prodrug or the liquid or reconstituted formulation of the present invention via topical, enteral or parenteral administration or by methods of external application, injection or infusion, including intraarticular, periarticular, intradermal, subcutaneous, intramuscular, intravenous, intraosseous, intraperitoneal, intrathecal, intracapsular, intraorbital, intravitreal, intratympanic, intravesical, intracardiac, transtracheal, subcuticular, subcapsular, subarachnoid, intraspinal, intraventricular, intrasternal injection or infusion, direct delivery to the brain via implanted device allowing delivery of the invention or the like to brain tissue or brain fluids (e.g., Ommaya Reservoir), direct intracerebroventricular injection or infusion, injection or infusion into brain or brain associated regions, injection into the subchoroidal space, retro-orbital injection and ocular instillation.

Preferably, the method comprises the step of administering the polymeric hGH prodrug or the liquid or reconstituted formulation of the present invention via injection, more preferably via subcutaneous injection.

In a preferred embodiment, the present invention relates to a polymeric hGH prodrug of the present invention, preferably the polymeric hGH prodrug of formula (IV), or the liquid or reconstituted formulation comprising at least one polymeric hGH prodrug of the present invention, preferably the polymeric hGH prodrug of formula (IV), for use in the treatment of GHD in children via subcutaneous injection.

Another aspect of the present invention is a container comprising the the polymeric hGH prodrug or the liquid or reconstituted formulation of the present invention via injection, preferably via subcutaneous injection.

Preferred containers are syringes, dual-chamber syringes, vials, vials with stopper and seal, ampoules, cartridges, and dual-chamber cartridges.

EXAMPLES

Cation Exchange Chromatography

The purification of conjugates by cation exchange chromatography was performed using an ÄKTA Pure system (GE Healthcare) equipped with a Macrocap SP column with a column volume of 279 mL. The respective reaction mixture was applied to the column which was pre-equilibrated in 20 mM sodium acetate, 10 mM L-methionine buffer, pH 4.0 (buffer A). After loading, the column was washed with three column volumes of buffer A to remove any unreacted PEG reagent. Mono-conjugates were eluted using a gradient of 0-30% buffer B (20 mM sodium acetate, 1 M sodium chloride, pH 4.5) over 15 column volumes. A gradient of 30-80% B over three column volumes was used to elute unreacted growth hormone. The column was cleaned with 3 column volumes of 100% buffer B. The flow rate was 20 mL/min for loading and 25 mL/min during the elution. The elution was monitored by detection at 280 nm.

SDS-PAGE Analysis

The mPEG-hGH conjugates were analysed by SDS-PAGE using NuPAGE® Novex 4-12% Bis-Tris gels (1.0 mm thick, 12 lanes), NuPAGE MOPS SDS-Running Buffer, HiMark™ Pre-stained High Molecular Weight Protein Standard and Coomassie Colloidal Blue™ Staining Kit (Invitrogen). In each lane 1 μg hGH eq. of the conjugate were applied and the electrophoresis and subsequent staining performed according to the supplier's protocol. Images of the gels were generated using a Digi Image System (Kisker Biotech) and a Power Shot G10 camera (Canon).

Dia-/Ultrafiltration

Dia- and Ultrafiltration steps were performed using a labscale TFF system (Millipore) equipped with Pellicon XL Biomax membranes with a membrane are of 50 cm² and a molecular weight cut-off of 5 or 10 kDa for hGH only, 10 kDa for 4× 10 kDa mPEG-linker-hGH monoconjugate 2 and 50 kDa for 4× 20 kDa mPEG-linker-hGH monoconjugate 1.

RP-HPLC

The following RP-HPLC parameters were used:

Mobile phase A was composed of 0.05% aqueous TFA and mobile phase B was composed of 0.04% TFA in acetonitrile. A Waters UPLC C18 BEH 300 Å 1.7 μm 2.1×50 mm column was used. Flow rate was set to 0.2-0.4 mL/min, detection was at a wavelength of 215 nm, the column running temperature was 30° C. (+5° C.). The autosampler temperature was set at 4° C. and the sample injection load was 20 μL. For peak separation the gradient shown in Table 1 was used.

TABLE 1

| RP-HPLC gradient | |
|---|---|
| Time [min] | % B |
| 0 | 25 |
| 1 | 25 |
| 8 | 40 |
| 30 | 60 |
| 30.1 | 90 |
| 30.5 | 90 |
| 30.6 | 25 |
| 35 | 25 |

Buffer Exchange

Buffer exchange was performed using an ÄKTA explorer system (GE Healthcare) equipped with a HiPrep 26/10 Desalting column or a HiTrap Desalting column.

Example 1: Synthesis of Transient 4× 20 kDa mPEG-Linker-hGH Monoconjugate 1 (Reference Substance; not According to the Invention)

1

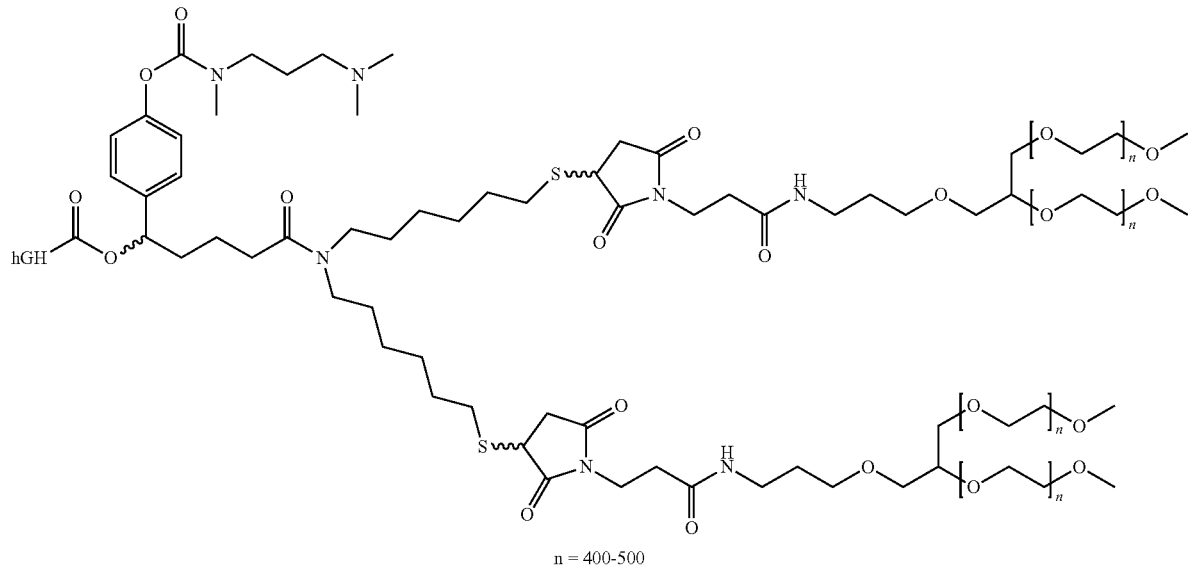

n = 400-500

4× 20 kDa mPEG-linker-hGH monoconjugate 1 was synthesized according to a similar procedure as described in WO2009/133137 A2. The formulations of 4× 20 kDa mPEG-linker-hGH monoconjugate 1 as shown in Table 2 were prepared.

TABLE 2

Formulations of 4× 20 kDa mPEG-linker-hGH monoconjugate 1

| Formulation name: | Concentration of 4× 20 kDa mPEG-linker-hGH monoconjugate 1 formulation [mg conjugate/mL] | Concentration of hGH eq. [mg hGH eq./mL] |
|---|---|---|
| 1A | 30 | 6 |
| 1B | 45 | 9 |
| 1C | 75 | 15 |

Example 2: Synthesis of High Strength Transient 4× 10 kDa mPEG-linker-hGH Monoconjugate 2

4× 10 kDa mPEG-linker-hGH monoconjugate 2 was synthesized according to a similar procedure as described in WO2009/133137 A2; in detail the manufacturing process was conducted as follows:

hGH was buffer exchanged to 100 mM sodium borate pH 9 and the concentration of hGH was adjusted to 10 mg/mL. A molar excess of 4-arm branched 40 kDa mPEG-pentafluorophenylcarbonate derivative relative to the amount of hGH was dissolved in water to form a 6% (w/w) reagent solution. The reagent solution was added to the hGH solution in a 1-to-1 ratio (based on weight) and mixed. The reaction mixture was incubated under stirring for 105 min at 12-16° C. and subsequently quenched by adding 4 volumes of a solution comprising 27 mM acetic acid and 12.5 mM L-methionine to 1 volume of the reaction mixture to lower the pH of the solution to 4-4.5. After sterile filtration, the reaction mixture was incubated at room temperature for 16±4 h. 4× 10 kDa mPEG-linker-hGH monoconjugate 2 was purified by cation exchange chromatography.

Buffer exchange and adjustment to the desired concentration of 4× 10 kDa mPEG-linker-hGH monoconjugate 2 was achieved using a tangential-flow filtration system. Herewith the eluate from the cation exchange chromatography was ultra-filtrated and dia-filtrated to formulation buffer (10 mM succinic acid, 85 g/L trehalose dihydrate, pH 5.0 with 1M Tris-solution). Using the same system the trehalose concentration was lowered to 65 g/L and the concentration of this stock solution adjusted to 105±3 mg/mL of 4× 10 kDa mPEG-linker-hGH monoconjugate 2 (corresponding to 35±1 mg hGH eq./mL). The formulations as shown in Table 3 were prepared based on this stock-solution of compound 2 by diluting the stock solution with high strength formulation buffer (10 mM succinic acid, 89 g/L trehalose dihydrate, adjusted to pH 5.0 with 1M Tris-base).

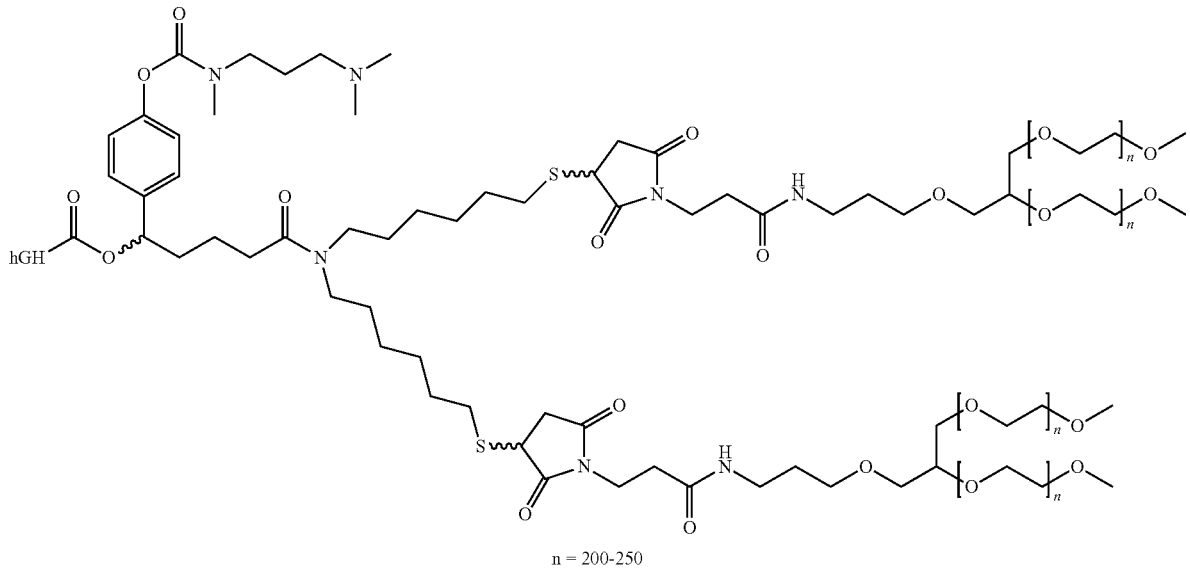

2 n = 200-250

TABLE 3

Formulations of 4× 10 kDa mPEG-linker-hGH monoconjugate 2

| Formulation name: | Concentration of 4× 10 kDa mPEG-linker-hGH monoconjugate 2 formulation [mg/mL] | Concentration of hGH eq. [mg hGH eq./mL] |
|---|---|---|
| 2A | 103.8 | 34.6 |
| 2B | 95.1 | 31.7 |
| 2C | 81.9 | 27.3 |
| 2D | 65.1 | 21.7 |
| 2E | 47.4 | 15.8 |

Individual batches were analyzed by RP-HPLC, SE-HPLC, peptide mapping and SDS-PAGE. SDS-PAGE showed that all formulation have comparable product qualities which are similar to the reference. During method development it was discovered that the load of the cation exchange chromatography column which is used to purify the 4× 10 kDa mPEG-linker-hGH monoconjugate 2 could be significantly increased compared to the purification procedure of 4× 20 kDa mPEG-linker-hGH monoconjugate 1.

Conclusion:

4× 10 kDa mPEG-linker-hGH monoconjugate 2 could by synthesized by implementing only minor changes to the manufacturing process compared to the manufacturing process described in EP-A 2113256 and showed improved handling and product properties. Loading of the CIEX column for purification could be at least tripled without impairing the separation efficacy and product quality. Additionally, the content of the final product could be increased to above 100 mg/mL of the 4× 10 kDa mPEG-linker-hGH-conjugate 2 which corresponds to approx. 35 mg hGH eq./mL.

Example 3: Syringability of High Strength Formulations of 4× 10 kDa mPEG-Linker-hGH Monoconjugate 2 Compared to 4× 20 kDa mPEG-Linker-hGH Monoconjugate 1

Individual formulations from example 1 & 2 were investigated for their ability of being injected through injection needles with various inner diameters. Tests were performed on a Mecmesin Multitest 1-d stand, equipped with measuring device BFG 200N and using the Emperor Lite software (Vers. no. 1.16-015). Tested injection needles comprised a 27 G needle 0.4×13 mm 27G×½" from BD (Ref 300635, Lot 101009), a 29 G needle, 0.33×13 mm from Transcoject, and a 30 G needle 0.30×12 mm, 30G×½", from Sterican (Lot 2 G13258811). The measuring device was setup to measure the force for pushing the plunger down for a given constant plunger speed. The applied plunger speeds which correspond to the applied injection speeds were as follows:

| Injection speed | 688 mm/min | 5 sec/mL | 12 mL/min |
| | 344 mm/min | 10 sec/mL | 6 mL/min |
| | 229 mm/min | 15 sec/mL | 4 mL/min |
| | 172 mm/min | 20 sec/mL | 3 mL/min |
| | 138 mm/min | 25 sec/mL | 2.4 mL/min |
| | 115 mm/min | 30 sec/mL | 2 mL/min |

Testing was performed using the following steps:

1. Charging of a 1 ml Luer-lok Syringe, (BD, Ref 309628) with sample (using a 20 G needle, 0.90×40 mm, 20G×1½" from Sterican)
2. Removal of air bubbles
3. Attachment of test needle (starting with the largest inner diameter) onto the syringe
4. Clamping the syringe into the holder
5. Selection of appropriate measuring settings
6. Start measurement and collect the sample in a glass vial (placed underneath the syringe)
7. Removal of syringe from holder
8. Re-charging of the syringe with test material and measuring of subsequent setting→these steps were repeated for all needles (with descending needle diameter) and for every test sample.

Formulation buffer without mPEG-linker-hGH monoconjugate 1 or 2 was used as reference solution.

For all different injection needles and for all injection speeds the injection forces were determined for 4× 10 kDa mPEG-linker-hGH monoconjugate 2 and compared with the results for 4× 20 kDa mPEG-linker-hGH monoconjugate 1. Table 4 shows the comparison of injection forces between 4× 10 kDa mPEG-linker-hGH monoconjugate 2 and 4× 20 kDa mPEG-linker-hGH monoconjugate 1 for the 27 G needle 0.4×13 mm 27G×½" from BD (Ref 300635, Lot 101009).

TABLE 4

Injection forces of 4x 10 kDa mPEG-linker-hGH monoconjugate 2 and 4x 20 kDa mPEG-linker-hGH monoconjugate 1 for a 27 G needle (0.4 × 13 mm 27 G × ½" from BD)

| | | Injection Force [N] | | | | | | | |
|---|---|---|---|---|---|---|---|---|---|
| Injection speed | Injection speed | Formulation of 4x 10 kDa mPEG-linker-hGH monoconjugate 2 | | | | | Formulation of 4x 20 kDa mPEG-linker-hGH monoconjugate 1 | | |
| [sec/mL] | [mL/min] | 2E | 2D | 2C | 2B | 2A | 1A | 1B | 1C |
| 5 | 12 | 5.35 | 7.35 | 9.65 | 22.0 | 30.0 | 6.6 | 12..1 | 20.3 |
| 10 | 6 | 2.90 | 4.00 | 4.90 | 11.35 | 16.0 | 3.6 | 6.5 | 10.7 |
| 15 | 4 | 2.05 | 2.95 | 3.75 | 7.95 | 10.8 | 2.7 | 4.6 | 7.5 |
| 20 | 3 | 1.60 | 2.40 | 3.15 | 6.15 | 8.85 | 2.2 | 3.8 | 5.7 |
| 25 | 2.4 | 1.45 | 2.05 | 2.65 | 5.05 | 7.35 | 1.8 | 3.2 | 4.5 |
| 30 | 2 | 1.30 | 1.70 | 2.25 | 4.45 | 6.40 | n.d. | n.d. | n.d. |

Table 5 shows the comparison of injection forces between 4× 10 kDa mPEG-linker-hGH monoconjugate 2 and 4× 20 kDa mPEG-linker-hGH monoconjugate 1 for the 29 G needle, 0.33× 13 mm from Transcoject.

TABLE 5

Injection forces of 4x 10 kDa mPEG-linker-hGH monoconjugate 2 and 4x 20 kDa mPEG-linker-hGH monoconjugate 1 for a 29 G needle (0.33 × 13 mm from Transcoject)

| Injection speed [sec/mL] | injection speed [mL/min] | Formulation of 4x 10 kDa mPEG-linker-hGH monoconjugate 2 | | | | | Formulation of 4x 20 kDa mPEG-linker-hGH monoconjugate 1 | | |
|---|---|---|---|---|---|---|---|---|---|
| | | 2E | 2D | 2C | 2B | 2A | 1A | 1B | 1C |
| 5 | 12 | 12.70 | 20.95 | 26.70 | 32.70 | n.d. | n.d. | 27.3 | n.d. |
| 10 | 6 | 6.40 | 10.05 | 13.25 | 16.90 | 25.40 | 12.0 | 14.9 | 28.6 |
| 15 | 4 | 4.40 | 6.90 | 9.20 | 11.50 | 19.20 | 8.0 | 10.6 | 20.2 |
| 20 | 3 | 3.70 | 5.30 | 6.75 | 8.95 | 13.95 | 6.3 | 7.9 | 15.2 |
| 25 | 2.4 | 2.80 | 4.40 | 5.70 | 7.50 | 11.50 | 5.0 | 6.5 | 12.3 |
| 30 | 2 | 2.50 | 3.70 | 4.65 | 6.05 | 10.05 | n.d. | n.d. | n.d. |

Table 6 shows the comparison of injection forces between 4× 10 kDa mPEG-linker-hGH monoconjugate 2 and 4× 20 kDa mPEG-linker-hGH monoconjugate 1 for the 30 G needle 0.30×12 mm, 30G×½", from Sterican (Lot 2 G13258811).

TABLE 6

Injection forces of 4x 10 kDa mPEG-linker-hGH monoconjugate 2 and 4x 20 kDa mPEG-linker-hGH monoconjugate 1 for a 30 G needle (0.30 × 12 mm, 30 G × ½", from Sterican)

| Injection speed [sec/mL] | injection speed [mL/min] | Formulation of 4x 10 kDa mPEG-linker-hGH monoconjugate 2 | | | | | Formulation of 4x 20 kDa mPEG-linker-hGH monoconjugate 1 | | |
|---|---|---|---|---|---|---|---|---|---|
| | | 2E | 2D | 2C | 2B | 2A | 1A | 1B | 1C |
| 5 | 12 | 26.6 | 28.50 | 50.90 | n.d. | n.d. | n.d. | 45.2 | * |
| 10 | 6 | 12.95 | 19.60 | 26.90 | 36.50 | n.d. | 15.0 | 25.5 | 51.0 |
| 15 | 4 | 8.40 | 13.70 | 18.90 | 25.20 | 34.7 | 10.3 | 17.7 | 37.6 |
| 20 | 3 | 7.00 | 10.50 | 13.90 | 19.50 | 28.2 | 8.2 | 13.1 | 28.9 |
| 25 | 2.4 | 5.50 | 8.05 | 11.20 | 15.70 | 20.6 | 7.0 | 10.5 | 23.4 |
| 30 | 2 | 4.75 | 7.50 | 9.50 | 13.15 | 17.5 | n.d. | n.d. | n.d. |

Conclusion:

The injectability of 4× 10 kDa mPEG-linker-hGH monoconjugate 2 was highly improved and the injection force could be reduced 3.5-fold to 4-5 fold compared to 4× 20 kDa mPEG linker-hGH monoconjugate 1.

Example 4: Viscosity Measurements of 4× 10 kDa mPEG-Linker-hGH Monoconjugate 2 Compared to 4× 20 kDa mPEG-Linker-hGH Monoconjugate 1

The dynamic viscosity of test samples was determined at Infrasery Knapsack (now synlab Pharma Institute) using a method according to EP method 2.2.10. All measurements were performed with approx. 1-5 mL of test sample at 23.0±0.1° C. using a cone/plate measuring system (CP50/1). The shearing rate was in the range of 100 $s^{-1}$-10 $s^{-1}$.

All tested formulations of 4× 10 kDa mPEG-linker-hGH monoconjugate 2 and 4× 20 kDa mPEG-linker-hGH monoconjugate 1 were adjusted to an equal osmolality of approx. 290 mOsmol/kg by increasing or decreasing the amount of trehalose in the formulation. The dynamic viscosity values measured for all test samples are summarized in Table 7.

TABLE 7

Dynamic viscosity values for different formulations of 4x 10 kDa mPEG-linker-hGH monoconjugate 2 and 4x 20 kDa mPEG-linker-hGH monoconjugate 1 which were adjusted to similar osmolalities.

| | Formulation: | Conc. [mg/mL] hGH eq.] | Content trehalose in formulation buffer [g/L] | Osmolality | Viscosity [mPa * s] |
|---|---|---|---|---|---|
| 4x 10 kDa mPEG-linker-hGH monoconjugate 2 | 2A | 34.6 | 65 | 286 | 25.6 |
| | 2B | 31.7 | 68 | 290 | 18.9 |
| | 2C | 27.3 | 71 | 286 | 14.9 |
| | 2D | 21.7 | 75 | 283 | 9.9 |
| | 2E | 15.8 | 78 | 284 | 6.0 |
| 4x 20 kDa mPEG-linker-hGH monoconjugate 1 | 1A | 6 | 85 | 291 | 7.4 |
| | 1B | 9 | 80 | 293 | 12.8 |
| | 1C | 15 | 70 | 285 | 31 |

Conclusion:

The dynamic viscosity of 4× 10 kDa mPEG-linker-hGH monoconjugate 2 could be significantly reduced about a factor of 4- to 5-fold compared to 4× 20 kDa mPEG linker-hGH monoconjugate 1.

Example 5: Reconstitution Time of Lyophilisates of 4× 10 kDa mPEG-linker-hGH Monoconjugate 2

1 mL of 4× 10 kDa mPEG-linker-hGH monoconjugate 2 was lyophilized in a Din2R vial and after lyophilization the lyo cake was dissolved with 1 mL water for injection. The reconstitution time was compared to the dissolution time of a lyophilisate of 4× 20 kDa mPEG-linker-hGH monoconjugate 1. During reconstitution more gas bubbles were detected for 4× 20 kDa mPEG-linker-hGH monoconjugate 1. While the dissolution of the lyo cake itself was quite fast, the time until a clear solution was obtained with only a minimal amount of gas bubbles remaining, was significantly shorter for 4× 10 kDa mPEG-linker-hGH monoconjugate 2. The results of this reconstitution procedure are summarized in Table 8.

TABLE 8

Reconstitution times of 4x 10 kDa mPEG-linker-hGH monoconjugate 2 and 4x 20 kDa mPEG-linker-hGH monoconjugate 1

| | 4x 10 kDa mPEG-linker-hGH monoconjugate 2 | 4x 20 kDa mPEG-linker-hGH monoconjugate 1 |
|---|---|---|
| Time for dissolution | <1 min | <1 min |
| Time until a clear solution is obtained | <5 min | >15 min |
| Time for disappearance of most air bubbles | <5 min | >15 min |

Conclusion:

The time of reconstitution until a clear and virtually bubble free solution is achieved is significantly shorter for 4× 10 kDa mPEG-linker-hGH monoconjugate 2 compared to 4× 20 kDa mPEG linker-hGH monoconjugate 1.

Example 6: In Vitro Hydrolysis of 4× 10 kDa mPEG-Linker-hGH Monoconjugate 2

For the determination of in vitro linker cleavage rates of 4× 10 kDa mPEG-linker-hGH monoconjugate 2 or 4× 20 kDa mPEG-linker-hGH monoconjugate 1, the compounds were buffer exchanged to PBST buffer at pH 7.4 and the eluted solutions were filtered through a 0.22 μm filter and incubated at 37° C. for 1 week. Samples were taken at certain time intervals and analyzed by RP-HPLC. All peaks were integrated and allocated and the relevant peak areas were plotted against incubation time. Curve fitting software was applied to determine first-order cleavage rates. Table 9 shows in vitro hydrolysis rates of 4× 10 kDa mPEG-linker-hGH monoconjugate 2 and 4× 20 kDa mPEG-linker-hGH monoconjugate 1 at pH 7.4 and 37° C.

TABLE 9

In vitro hydrolysis rates of 4x 10 kDa mPEG-linker-hGH monoconjugate 2 or 4x 20 kDa mPEG-linker-hGH monoconjugate 1 at pH 7.4 and 37° C.

| | Half life time [h] | 95% confidence interval [h] |
|---|---|---|
| 4x 10 kDa mPEG-linker-hGH monoconjugate 2 | 104.7 | 90.70-123.8 |
| 4x 20 kDa mPEG-linker-hGH monoconjugate 1 | 107.2 | 91.89-128.6 |

Conclusion:

The in vitro hydrolysis rates of conjugates 1 and 2 at pH 7.4 and 37° C. were in the range of 105±5 h. Both half life times were highly comparable and lay within the 95% confidence interval.

Example 7: Quantification of Conjugates 1 and 2 in Serum Samples from Animal Studies An ELISA based method was used to quantify conjugates 1 and 2 in serum samples from animal studies. The same sandwich ELISA format was used for both conjugates 1 and 2, which utilized a sheep anti-hGH polyclonal antibody (Abcam, Cat. No. ab64499) as capture antibody and a biotinylated rabbit anti-PEG antibody (Epitomics, Cat. No. 2137-1) as detection antibody. Read-out was done with streptavidin-HRP (Jackson ImmunoResearch, Cat, No. 016-030-084) and a commercial TMB liquid substrate system (Sigma, Cat. No. T0440), Serum standards and samples were diluted 1:50 with a pH 7.0 buffer (50 mM HEPES, 1 mM $CaCl_2$, 0.05% Tween-20 and 1% BSA) prior to measurement. Sample incubation on the ELISA plate was performed under shaking for 2 h at 37° C.

Example 8: Quantification of Total mPEG40 and 80 in Serum Samples from Animal Studies An ELISA based method was used to quantify mPEG40 and mPEG80 in serum samples from animal studies. The same sandwich ELISA format was used for both analytes mPEG40 and mPEG80, which utilized an anti-PEG (methoxy group) rabbit monoclonal antibody, (Epitomics, Cat. No. 2061-1) as capture antibody and a biotinylated anti-PEG mouse monoclonal IgM antibody (ANP Tech, Cat. No. 90-1052) as detection antibody. Read-out was done with streptavidin-HRP (Jackson ImmunoResearch, Cat. No. 016-030-084) and a commercial TMB liquid substrate system (Sigma, Cat. No. T0440). Serum standards and samples were diluted 1:50 with a pH 7.0 buffer (50 mM HEPES, 1 mM $CaCl_2$, 0.05% Tween-20 and 1% BSA) prior to measurement. Sample incubation on the ELISA plate was performed under shaking for 2 h at 37° C.

Example 9: Comparative Pharmacokinetic Study in Cynomolgus Monkeys Treated with Conjugates 1 and 2

Two groups of five healthy male non-nave cynomolgus monkeys each received a single subcutaneous administration of conjugate 1 or a single subcutaneous administration of conjugate 2 at a target dose level of 1 mg hGH equivalents per kg (corresponding to 3 mg conjugate 2/kg and 5 mg conjugate 1/kg, respectively). For PK-determinations blood samples were collected up to 336 hours post dose and serum generated thereof (for mPEG quantification serum samples were collected up to 56 days). Pharmacokinetic analysis according to Example 7 indicated that both compounds effected a comparable maximal conjugate level (9,200 ng hGH equivalents/mL for conjugate 1 and 7,400 ng hGH equivalents/mL for conjugate 2) which was reached around 36 hours post dosing. mPEG concentration levels were determined according to Example 8. Both mPEG PK-profiles had their maximum concentration levels at 48 hours post dosing. Clearance of mPEG40 was faster than for mPEG80 as indicated in the terminal elimination half lifes (300 h for mPEG80 and 260 h for mPEG40). This resulted in an overall significant lower mPEG exposure for conjugate 2 over conjugate 1 in this comparative PK-study.

Abbreviations:

AIDS acquired immunodeficiency syndrome

CRI chronic renal insufficiency

DF Diafiltration

ELISA Enzyme linked immunosorbent assay

EP European Pharmacopoeia
eq stoichiometric equivalent
G gauge
ED
HIV human immunodeficiency virus
ISS idiopathic short stature
MW molecular weight
NS Noonan syndrome
PEG polyethylene glycol
PWS Prader-Willi syndrome
PK Pharmacokinetic
RP-HPLC reversed-phase high performance liquid chromatography
rt room temperature
SBS short bowel syndrome
SDS-PAGE sodium dodecyl sulfate polyacrylamid gel electrophoresis
SEC size exclusion chromatography
SHOX short stature hoeobox
SGA small for gestational age
TFF Tangential flow filtration
Tris tris(hydroxymethyl)aminomethane
TS Turner syndrome
UF Ultrafiltration

The invention claimed is:

1. A polymeric human growth hormone (hGH) prodrug or a pharmaceutically acceptable salt thereof of formula (Ia) or (Ib):

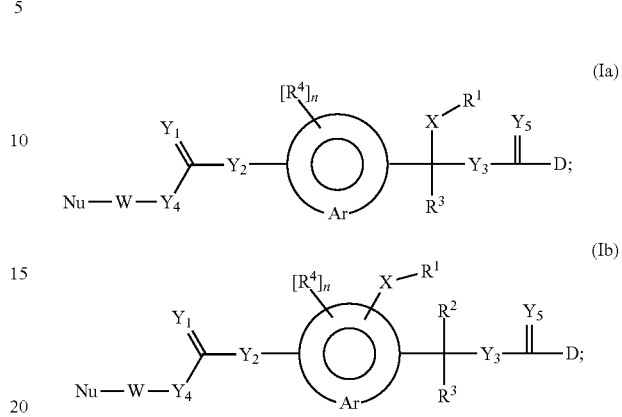

```
SEQUENCE LISTING

<160> NUMBER OF SEQ ID NOS: 1

<210> SEQ ID NO 1
<211> LENGTH: 191
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
``` wherein:
- -D is a hGH moiety connected to the rest of the molecule through an amine functional group;
- n is 0, 1, 2, 3, or 4;
- —X— is a chemical bond or a spacer;
- =$Y_1$, is selected from the group consisting of =O and =S;
- —$Y_2$— is selected from the group consisting of —O— and —S—;
- —$Y_3$— and —$Y_5$— are independently of each other selected from the group consisting of —O— and —S—;
- —$Y_4$— is selected from the group consisting of —O—, —$NR^5$— and —$C(R^6R^{6a})$—;
- —$R^1$ comprises a moiety of formula-(IIc):

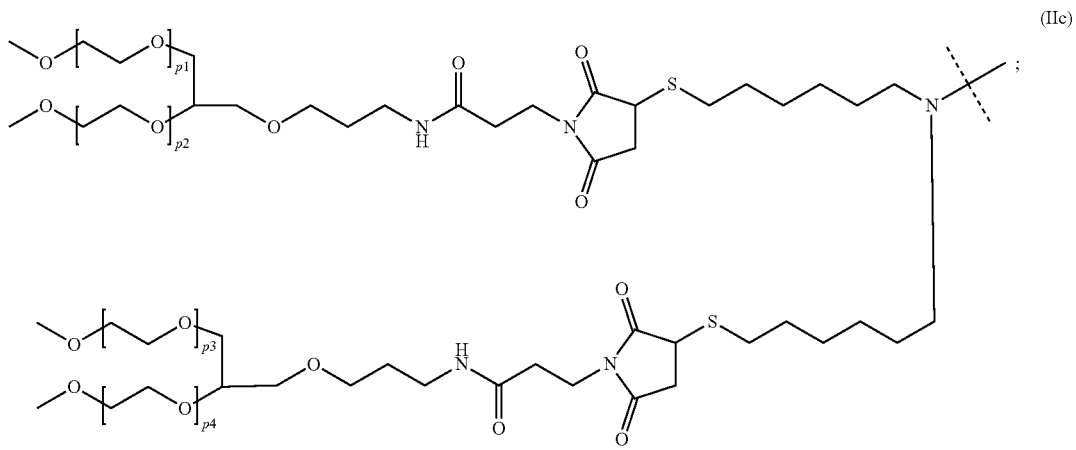

(IIc)

wherein:
- p1, p2, p3, and p4 are independently an integer ranging from 180 to 240;
- —$R^2$, —$R^3$, —$R^5$, —$R^6$, and —$R^{6a}$ are independently of each other selected from the group consisting of -H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
- —$R^4$ is selected from the group consisting of methyl, ethyl, n-propyl, isopropyl, n-butyl, isobutyl, sec-butyl, tent-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
- —W— is selected from the group consisting of $C_{1-20}$ alkyl optionally interrupted by one or more groups selected from the group consisting of $C_{3-10}$ cycloalkyl, 8- to 30-membered carbopolycyclyl, 3- to 10-membered heterocyclyl, —C(O)—, —$C(O)N(R^7)$—, —O—, —S—, and —$N(R^7)$—;
- —Nu is a nucleophile selected from the group consisting of —$N(R^7R^{7a})$, —$N(R^7R^{7a})$, —$N(R^7OH)$, —$N(R^7)$—$N(R^{7a}R^{7b})$,

—$S(R^7)$, —COOH,

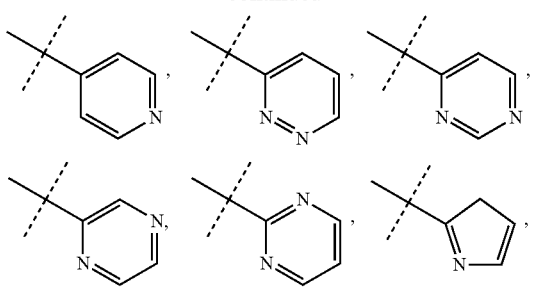

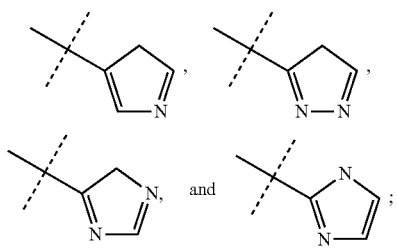

—Ar— is selected from the group consisting of

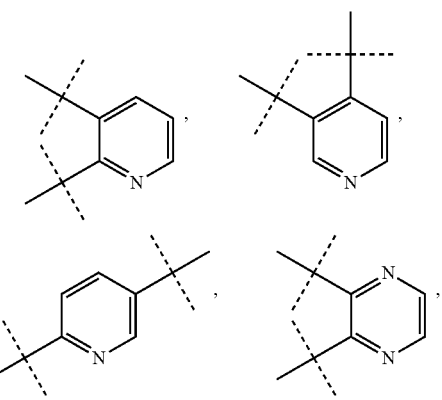

-continued

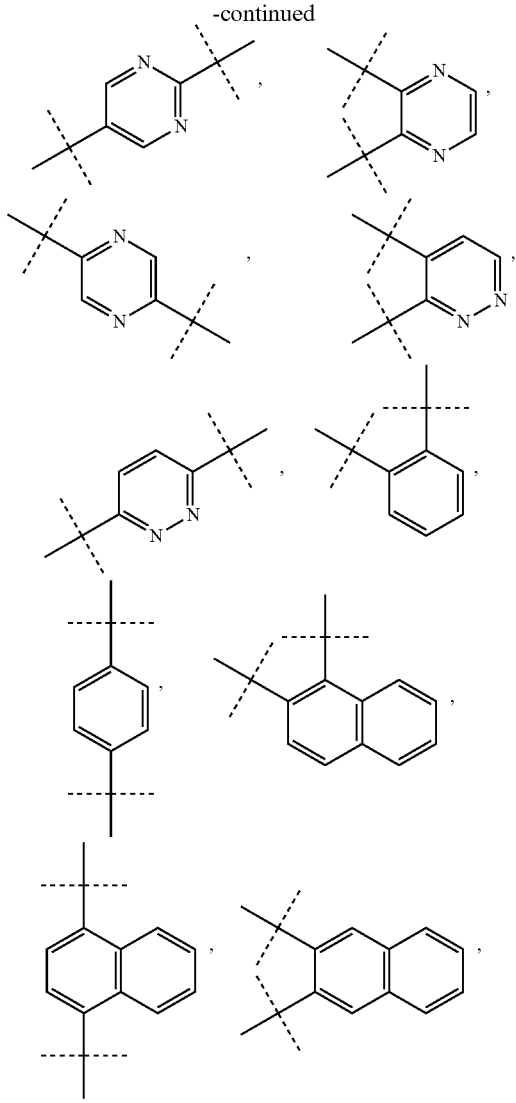

-continued wherein:
dashed lines indicate attachment to the rest of the prodrug,
—$Z^1$— is selected from the group consisting of —O—, —S— and —N($R^7$)—, and
—$Z^2$— is —N($R^7$)—; and
—$R^7$, —$R^{7a}$, and —$R^{7b}$ are independently of each other selected from the group consisting of —H, $C_{1-6}$ alkyl, $C_{2-6}$ alkenyl and $C_{2-6}$ alkynyl; and
wherein the prodrug of formula (Ia) and (Ib) is optionally further substituted.

2. The prodrug of claim 1;
wherein the polymeric hGH prodrug is of formula (IV):

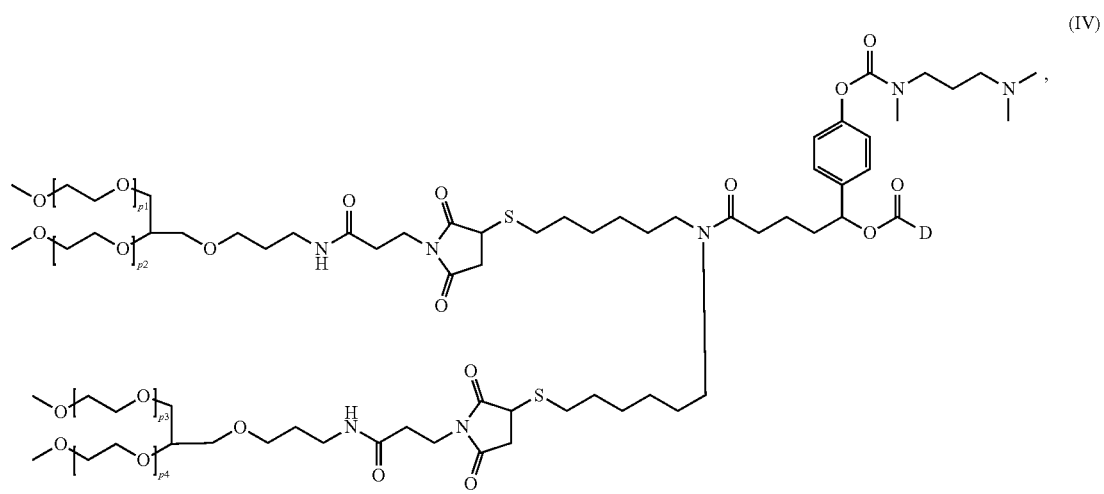

(IV)

wherein:
D is an hGH moiety connected to the rest of the molecule through an amine functional group; and
p1, p2, p3, and p4 are independently an integer ranging from 180 to 240.

3. A pharmaceutical formulation comprising: the prodrug of claim 1; and at least one excipient.

4. The pharmaceutical formulation of claim 3; wherein the pharmaceutical formulation is a dry formulation and comprises from 1 to 99.9% (w/w) of the prodrug.

5. The dry pharmaceutical formulation of claim 3;
wherein the dry formulation is obtained by a process comprising the steps of:
(a) providing a liquid formulation comprising:
3-300 mg/ml or the polymeric hGH prodrug
5-50 mM of succinic acid; and
optionally 25-150 mg/ml of trehalose dihydrate;
wherein the liquid formulation has a pH ranging from pH 4.0 to pH 6.0,
which is titrated using a suitable buffer; and
(b) drying the liquid formulation of step (a).

6. The dry pharmaceutical formulation of claim 3;
wherein the dry formulation comprises:
14-65% (w/w) of the polymeric hGH prodrug;
0.5-2.5% (w/w) of succinic acid;
31-84% (w/w) of trehalose dihydrate; and
0.4-4% (w/w) of Tris.

7. A method of preparing a reconstituted formulation, wherein the method comprises the step of:
contacting the dry pharmaceutical formulation of claim 4 with a reconstitution solution.

8. A reconstituted formulation obtained from the method of claim 7.

9. The reconstituted formulation of claim 8;
wherein the reconstituted formulation comprises:
3-300 mg/ml of the polymeric hGH prodrug;
5-50 mM of succinic acid;
25-150 mg/ml of trehalose dihydrate; and
Tris 1-50 mM; and
wherein the reconstituted formulation has a pH ranging from pH 4.0 to pH 6.0.

10. A method of treating, controlling, delaying, or preventing in a mammalian patient in need of the treatment, control, delay, or prevention of at least one diseases which can be treated, controlled, delayed, or prevented with hGH, wherein the method comprises:
a step of administering to said patient a therapeutically effective amount of the prodrug of claim 1.

11. The method of claim 10;
wherein the administration is via topical, enteral, or parenteral administration, or is by external application, injection, or infusion, direct delivery to the brain via implanted device allowing delivery of the invention or the like to brain tissue or brain fluids, direct intracerebroventricular injection or infusion, injection or infusion into brain or brain associated regions, injection into the subchoroidal space, retro-orbital injection, or ocular instillation.

12. The method of claim 11;
wherein the administration is by intraarticular, periarticular, intradermal, subcutaneous, intramuscular, intravenous, intraosseous, intraperitoneal, intrathecal, intracapsular, intraorbital, intravitreal, intratympanic, intravesical, intracardiac, transtracheal, subcuticular, subcapsular, subarachnoid, intraspinal, intraventricular, or infrasternal injection or infusion.

13. The method of claim 10;
wherein the disease is selected from the group consisting of growth hormone deficiency in children, idiopathic short stature, short stature homeobox gene mutations, Turner syndrome, Noonan syndrome, Prader-Willi syndrome, children born small for gestational age, chronic renal insufficiency, growth hormone deficiency in adults, wasting due to HIV or AIDS or other malignancies, short bowel syndrome, sarcopenia, and frailty.

14. The method of claim 10, wherein the disease is growth hormone deficiency in children.

15. The prodrug of claim 1, wherein the -D is a hGH moiety of SEQ ID NO:1.

16. The prodrug of claim 2, wherein -D is connected to the rest of the molecule through an amine provided by a lysine side chain.

17. The prodrug of claim 2, wherein -D is a hGH moiety having the sequence of SEQ ID NO:1.

18. The pharmaceutical formulation of claim 3, wherein the pharmaceutical formulation is a liquid formulation and comprises from 3 to 300 mg/ml of the prodrug.

19. The liquid pharmaceutical formulation of claim 18; wherein the liquid formulation comprises 3-300 mg/ml of the polymeric hGH prodrug; 5- 50 mM of succinic acid; optionally 25-150 mg/ml of trehalose dihydrate; and optionally 1- 50 mM of methionine; and wherein the liquid formulation has a pH ranging from pH 4.0 to 6.0, which is titrated using a suitable buffer.

20. The prodrug of claim 1;
wherein p1, p2, p3, and p4 are independently an integer ranging from 200 to 240.

21. The prodrug of claim 2;
wherein p1, p2, p3, and p4 are independently an integer ranging from 200 to 240.

* * * * *

UNITED STATES PATENT AND TRADEMARK OFFICE
CERTIFICATE OF CORRECTION

PATENT NO. : 10,799,563 B2
APPLICATION NO. : 15/527744
DATED : October 13, 2020
INVENTOR(S) : Thomas Kurpiers et al.

It is certified that error appears in the above-identified patent and that said Letters Patent is hereby corrected as shown below:

In the Specification

Column 4, Line 15, delete:

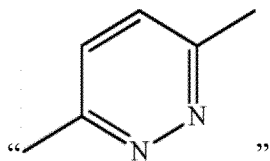

And replace with:

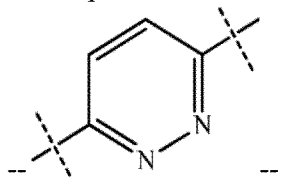

In the Claims

In Claim 1, at Column 55, Lines 6–12, delete:
"$=Y_1$, is selected from the group consisting of =0 and =S;
$-Y_2-$ is selected from the group consisting of –0–
and –S–;
$-Y_3-$ and $-Y_5-$ are independently of each other
selected from the group
consisting of –0– and –S–;
$-Y_4-$ is selected from the group consisting of –0–,"

And replace with:
--$=Y_1$ is selected from the group consisting of =O and =S;
$-Y_2-$ is selected from the group consisting of –O–

Signed and Sealed this
Fifteenth Day of November, 2022

Katherine Kelly Vidal
*Director of the United States Patent and Trademark Office* and $-S-$;

$-Y_3-$ and $-Y_5-$ are independently of each other selected from the group consisting of $-O-$ and $-S-$;

$-Y_4-$ is selected from the group consisting of $-O-$,--